United States Patent
Harry et al.

(10) Patent No.: US 9,616,234 B2
(45) Date of Patent: Apr. 11, 2017

(54) SYSTEM AND METHOD FOR NEURO-STIMULATION

(71) Applicant: TRUSTEES OF BOSTON UNIVERSITY, Boston, MA (US)

(72) Inventors: Jason D. Harry, Rumford, RI (US);
James B. Niemi, Chepachet, RI (US);
Scott Kellogg, Mattapoisett, MA (US);
Susan D'Andrea, Barrington, RI (US)

(73) Assignee: Trustees of Boston University, Boston, MA (US)

( * ) Notice: Subject to any disclaimer, the term of this patent is extended or adjusted under 35 U.S.C. 154(b) by 146 days.

(21) Appl. No.: 14/249,856

(22) Filed: Apr. 10, 2014

(65) Prior Publication Data

US 2014/0364678 A1    Dec. 11, 2014

Related U.S. Application Data

(63) Continuation of application No. 11/927,597, filed on Oct. 29, 2007, now abandoned, which is a
(Continued)

(51) Int. Cl.
*A61N 1/36*    (2006.01)
*A61H 23/02*    (2006.01)
(Continued)

(52) U.S. Cl.
CPC ........ *A61N 1/36164* (2013.01); *A61F 5/0026* (2013.01); *A61H 23/0263* (2013.01);
(Continued)

(58) Field of Classification Search
CPC ................................................ A61N 1/36103
(Continued)

(56) References Cited

U.S. PATENT DOCUMENTS

| 792,162 A | 6/1905 | Potter |
| 3,735,756 A | 5/1973 | Richards et al. |

(Continued)

FOREIGN PATENT DOCUMENTS

| CA | 2 484 880 | 4/2006 | |
| DE | 4211311 | 10/1993 | ............. A63F 13/08 |

(Continued)

OTHER PUBLICATIONS

Merriam-Webster Online Dictionary, http://www.webster.com, defined: *Sensorimotor*.

(Continued)

*Primary Examiner* — Alyssa M Alter
(74) *Attorney, Agent, or Firm* — Nixon Peabody LLP

(57) ABSTRACT

A neuro-stimulation system employs a includes a stimulator which may include electrode devices and/or vibration elements. A controller may be employed to drive the stimulating elements with an electrical signal. In response to the electrical signal, the stimulating elements deliver electrical and/or mechanical stimulation to the body part. The stimulation may be an aperiodic stimulation and/or may be a subthreshold stimulation. In one embodiment, the stimulator is disposable and the processor determines usage of the stimulator and ensures that the stimulator is limited to a certain amount of use. Neuro-stimulation systems may be applied to sensory cells of body parts during movement of the body parts to induce neuroplastic changes. Such movement may involve a variety of therapeutic applications, e.g. in stroke patient therapy.

6 Claims, 26 Drawing Sheets

Related U.S. Application Data continuation-in-part of application No. 10/429,252, filed on May 5, 2003, now Pat. No. 7,349,739.

(60) Provisional application No. 60/377,202, filed on May 3, 2002, provisional application No. 60/880,026, filed on Jan. 12, 2007.

(51) Int. Cl.

| | | |
|---|---|---|
| *A61N 1/04* | (2006.01) | |
| *A61F 5/00* | (2006.01) | |
| *A61N 1/05* | (2006.01) | |
| *A61N 2/00* | (2006.01) | |
| *A61N 1/32* | (2006.01) | |
| *A61N 1/362* | (2006.01) | |

(52) U.S. Cl.
CPC ......... *A61N 1/0452* (2013.01); *A61N 1/0456* (2013.01); *A61N 1/0472* (2013.01); *A61N 1/0484* (2013.01); *A61N 1/0556* (2013.01); *A61N 1/3601* (2013.01); *A61N 1/36003* (2013.01); *A61N 1/36007* (2013.01); *A61N 1/36014* (2013.01); *A61N 1/36071* (2013.01); *A61N 2/006* (2013.01); *A61H 2201/165* (2013.01); *A61H 2201/5007* (2013.01); *A61H 2201/5023* (2013.01); *A61H 2201/5043* (2013.01); *A61H 2201/5058* (2013.01); *A61N 1/0464* (2013.01); *A61N 1/0476* (2013.01); *A61N 1/0492* (2013.01); *A61N 1/321* (2013.01); *A61N 1/36017* (2013.01); *A61N 1/3627* (2013.01)

(58) Field of Classification Search
USPC ....................................................... 607/48, 3
See application file for complete search history.

(56) References Cited

U.S. PATENT DOCUMENTS

| | | | |
|---|---|---|---|
| 3,881,495 A | 5/1975 | Pannozzo et al. | |
| 4,105,017 A | 8/1978 | Ryaby et al. | |
| 4,308,868 A | 1/1982 | Jhabvala | |
| 4,664,118 A | 5/1987 | Batters | |
| 4,774,967 A | 10/1988 | Zanakis et al. | |
| 4,811,742 A | 3/1989 | Hassel et al. | |
| 4,832,033 A | 5/1989 | Maher et al. | |
| 4,862,359 A | 8/1989 | Trivedi et al. | |
| 4,890,618 A | 1/1990 | Weber et al. | |
| 4,919,140 A | 4/1990 | Borgens et al. | |
| 5,188,104 A | 2/1993 | Wernicke et al. | |
| 5,215,086 A | 6/1993 | Terry, Jr. et al. | |
| 5,231,988 A | 8/1993 | Wernicke et al. | |
| 5,269,303 A | 12/1993 | Wernicke et al. | |
| 5,273,033 A | 12/1993 | Hoffman | |
| 5,299,569 A | 4/1994 | Wernicke et al. | |
| 5,330,515 A | 7/1994 | Rutecki et al. | |
| 5,335,657 A | 8/1994 | Terry, Jr. et al. | |
| 5,360,438 A | 11/1994 | Fisher | |
| 5,397,338 A | 3/1995 | Grey et al. | |
| 5,487,759 A | 1/1996 | Bastyr et al. | |
| 5,514,175 A | 5/1996 | Kim et al. | |
| 5,562,717 A | 10/1996 | Tippey et al. | |
| 5,593,432 A | 1/1997 | Crowther et al. | |
| 5,620,483 A | 4/1997 | Minogue | |
| 5,707,400 A | 1/1998 | Terry, Jr. et al. | |
| 5,782,873 A * | 7/1998 | Collins ..................... | A61F 7/00 607/2 |
| 5,782,874 A | 7/1998 | Loos | |
| 5,792,187 A | 8/1998 | Adams | |
| 5,797,966 A | 8/1998 | Bontoux et al. | |
| 5,899,922 A | 5/1999 | Loos | |
| 6,032,074 A | 2/2000 | Collins | |
| 6,065,154 A | 5/2000 | Hulings et al. | |
| 6,078,838 A | 6/2000 | Rubinstein | |
| 6,095,148 A | 8/2000 | Shastri et al. | |
| 6,104,956 A * | 8/2000 | Naritoku ............ | A61N 1/36082 607/45 |
| 6,169,924 B1 | 1/2001 | Meloy et al. | |
| 6,205,359 B1 | 3/2001 | Boveja | |
| 6,208,902 B1 | 3/2001 | Boveja | |
| 6,272,383 B1 | 8/2001 | Grey et al. | |
| 6,366,814 B1 | 4/2002 | Boveja et al. | |
| 6,505,075 B1 | 1/2003 | Weiner | |
| 6,564,102 B1 | 5/2003 | Boveja | |
| 6,587,719 B1 | 7/2003 | Barrett et al. | |
| 6,611,715 B1 | 8/2003 | Boveja | |
| 6,615,081 B1 | 9/2003 | Boveja | |
| 6,650,943 B1 | 11/2003 | Whitehurst et al. | |
| 6,662,051 B1 | 12/2003 | Eraker et al. | |
| 6,665,562 B2 | 12/2003 | Gluckman et al. | |
| 6,668,191 B1 | 12/2003 | Boveja | |
| 6,741,895 B1 | 5/2004 | Gafni et al. | |
| 6,862,479 B1 | 3/2005 | Whitehurst et al. | |
| 6,871,099 B1 | 3/2005 | Whitehurst et al. | |
| 6,873,872 B2 | 3/2005 | Gluckman et al. | |
| 6,978,787 B1 | 12/2005 | Broniatowski | |
| 7,006,870 B1 | 2/2006 | Whitehurst et al. | |
| 7,039,466 B1 | 5/2006 | Harrison et al. | |
| 7,054,689 B1 | 5/2006 | Whitehurst et al. | |
| 7,062,330 B1 | 6/2006 | Boveja et al. | |
| 7,123,961 B1 | 10/2006 | Kroll et al. | |
| 2001/0003799 A1 | 6/2001 | Boveja | |
| 2001/0029391 A1 | 10/2001 | Gluckman et al. | |
| 2002/0042642 A1 | 4/2002 | Gerber | |
| 2002/0077688 A1 | 6/2002 | Kirkland | |
| 2002/0077689 A1 | 6/2002 | Kirkland | |
| 2002/0087192 A1 | 7/2002 | Barrett et al. | |
| 2002/0087201 A1 * | 7/2002 | Firlik ................... | A61N 1/0531 607/45 |
| 2002/0198572 A1 | 12/2002 | Weiner | |
| 2003/0004553 A1 | 1/2003 | Grill et al. | |
| 2003/0023282 A1 | 1/2003 | Barrett et al. | |
| 2003/0040071 A1 | 2/2003 | Terry, Jr. et al. | |
| 2003/0055476 A1 | 3/2003 | Vinup et al. | |
| 2003/0100924 A1 | 5/2003 | Foreman et al. | |
| 2003/0114886 A1 | 6/2003 | Gluckman et al. | |
| 2003/0120323 A1 | 6/2003 | Meadows et al. | |
| 2003/0144709 A1 | 7/2003 | Zabara et al. | |
| 2003/0216792 A1 | 11/2003 | Levin et al. | |
| 2003/0236558 A1 | 12/2003 | Whitehurst et al. | |
| 2004/0024428 A1 | 2/2004 | Barrett et al. | |
| 2004/0039427 A1 | 2/2004 | Barrett et al. | |
| 2004/0073271 A1 | 4/2004 | Harry et al. | |
| 2004/0073273 A1 | 4/2004 | Gluckman et al. | |
| 2004/0088021 A1 | 5/2004 | Cameron et al. | |
| 2004/0116995 A1 | 6/2004 | Dadd | |
| 2004/0122477 A1 | 6/2004 | Whitehurst et al. | |
| 2004/0147975 A1 | 7/2004 | Popovic et al. | |
| 2004/0162590 A1 | 8/2004 | Whitehurst et al. | |
| 2004/0171971 A1 | 9/2004 | Ravikumar et al. | |
| 2004/0172085 A1 | 9/2004 | Knudson et al. | |
| 2004/0173220 A1 | 9/2004 | Harry et al. | |
| 2004/0193228 A1 | 9/2004 | Gerber | |
| 2004/0214790 A1 | 10/2004 | Borgens | |
| 2004/0230255 A1 | 11/2004 | Dobak, III | |
| 2005/0004625 A1 | 1/2005 | Chow | |
| 2005/0010260 A1 | 1/2005 | Gerber | |
| 2005/0010265 A1 | 1/2005 | Fassio et al. | |
| 2005/0015117 A1 | 1/2005 | Gerber | |
| 2005/0033372 A1 | 2/2005 | Gerber | |
| 2005/0033373 A1 | 2/2005 | Gerber | |
| 2005/0033374 A1 | 2/2005 | Gerber | |
| 2005/0038484 A1 | 2/2005 | Knudson et al. | |
| 2005/0049655 A1 | 3/2005 | Boveja et al. | |
| 2005/0055065 A1 | 3/2005 | Campbell | |
| 2005/0060005 A1 | 3/2005 | Boggs, II et al. | |
| 2005/0070969 A1 | 3/2005 | Gerber | |
| 2005/0070970 A1 | 3/2005 | Knudson et al. | |
| 2005/0070974 A1 | 3/2005 | Knudson et al. | |
| 2005/0075678 A1 | 4/2005 | Faul | |
| 2005/0085866 A1 | 4/2005 | Tehrani | |
| 2005/0085874 A1 | 4/2005 | Davis et al. | |

(56) References Cited

U.S. PATENT DOCUMENTS

| | | |
|---|---|---|
| 2005/0107655 A1 | 5/2005 | Holzner |
| 2005/0113877 A1 | 5/2005 | Spinelli et al. |
| 2005/0113878 A1 | 5/2005 | Gerber |
| 2005/0119713 A1 | 6/2005 | Whitehurst et al. |
| 2005/0119714 A1 | 6/2005 | Sieracki et al. |
| 2005/0124848 A1 | 6/2005 | Holzner |
| 2005/0131467 A1 | 6/2005 | Boveja et al. |
| 2005/0131486 A1 | 6/2005 | Boveja et al. |
| 2005/0131493 A1 | 6/2005 | Boveja et al. |
| 2005/0137644 A1 | 6/2005 | Boveja et al. |
| 2005/0143783 A1 | 6/2005 | Boveja et al. |
| 2005/0143789 A1 | 6/2005 | Whitehurst et al. |
| 2005/0149146 A1 | 7/2005 | Boveja et al. |
| 2005/0182450 A1 | 8/2005 | Hunter et al. |
| 2005/0182453 A1 | 8/2005 | Whitehurst et al. |
| 2005/0182455 A1 | 8/2005 | Thrope et al. |
| 2005/0187586 A1 | 8/2005 | David et al. |
| 2005/0187590 A1 | 8/2005 | Boveja et al. |
| 2005/0192644 A1 | 9/2005 | Boveja et al. |
| 2005/0192645 A1 | 9/2005 | Stein et al. |
| 2005/0197678 A1 | 9/2005 | Boveja et al. |
| 2005/0203600 A1 | 9/2005 | Wallace et al. |
| 2005/0203601 A1 | 9/2005 | Palanker et al. |
| 2005/0209651 A1 | 9/2005 | Cameron et al. |
| 2005/0209652 A1 | 9/2005 | Whitehurst et al. |
| 2005/0209654 A1 | 9/2005 | Boveja et al. |
| 2005/0216070 A1 | 9/2005 | Boveja et al. |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0240243 A1 | 10/2005 | Barolat et al. |
| 2005/0240244 A1 | 10/2005 | Leinders et al. |
| 2005/0245989 A1 | 11/2005 | Davis |
| 2005/0246004 A1 | 11/2005 | Cameron et al. |
| 2005/0246006 A1 | 11/2005 | Daniels |
| 2005/0251216 A1 | 11/2005 | Hill et al. |
| 2005/0251220 A1 | 11/2005 | Barrett et al. |
| 2005/0251222 A1 | 11/2005 | Barrett et al. |
| 2005/0259454 A1 | 11/2005 | Varrichio et al. |
| 2005/0267542 A1 | 12/2005 | David et al. |
| 2005/0267545 A1 | 12/2005 | Cory |
| 2005/0277998 A1 | 12/2005 | Tracey et al. |
| 2005/0277999 A1 | 12/2005 | Strother et al. |
| 2005/0278000 A1 | 12/2005 | Strother et al. |
| 2005/0283202 A1 | 12/2005 | Gellman |
| 2006/0004421 A1 | 1/2006 | Bennett et al. |
| 2006/0004423 A1 | 1/2006 | Boveja et al. |
| 2006/0004429 A1 | 1/2006 | Mrva et al. |
| 2006/0009815 A1 | 1/2006 | Boveja et al. |
| 2006/0015154 A1 | 1/2006 | Zou et al. |
| 2006/0020297 A1 | 1/2006 | Gerber et al. |
| 2006/0020299 A1 | 1/2006 | Shalev |
| 2006/0025820 A1 | 2/2006 | Philips et al. |
| 2006/0129218 A1 | 6/2006 | Swoyer et al. |
| 2006/0155333 A1 | 7/2006 | Goetz |
| 2006/0155341 A1 | 7/2006 | Tehrani et al. |
| 2006/0155551 A1 | 7/2006 | Ueda |
| 2006/0167497 A1 | 7/2006 | Armstrong et al. |
| 2006/0167498 A1 | 7/2006 | DiLorenzo |
| 2006/0167523 A1 | 7/2006 | Tehrani et al. |
| 2006/0167524 A1 | 7/2006 | Kimura et al. |
| 2006/0173493 A1 | 8/2006 | Armstrong et al. |
| 2006/0173495 A1 | 8/2006 | Armstrong et al. |
| 2006/0173507 A1 | 8/2006 | Mrva et al. |
| 2006/0178703 A1 | 8/2006 | Huston et al. |
| 2006/0189839 A1 | 8/2006 | Laniado et al. |
| 2006/0190053 A1 | 8/2006 | Dobak, III |
| 2006/0190057 A1 | 8/2006 | Reese |
| 2006/0190061 A1 | 8/2006 | Stypulkowski |
| 2006/0194724 A1 | 8/2006 | Whitehurst et al. |
| 2006/0195143 A1 | 8/2006 | McClure et al. |
| 2006/0195146 A1 | 8/2006 | Tracey et al. |
| 2006/0195152 A1 | 8/2006 | Gerber |
| 2006/0195153 A1 | 8/2006 | DiUbaldi et al. |
| 2006/0195155 A1 | 8/2006 | Firlik et al. |
| 2006/0195158 A1 | 8/2006 | Cory |
| 2006/0195169 A1 | 8/2006 | Gross et al. |
| 2006/0195170 A1 | 8/2006 | Cohen et al. |
| 2006/0200206 A1 | 9/2006 | Firlik et al. |
| 2006/0200208 A1 | 9/2006 | Terry, Jr. et al. |
| 2006/0206164 A1 | 9/2006 | Gavronsky |
| 2006/0206165 A1 | 9/2006 | Jaax et al. |
| 2006/0206166 A1 | 9/2006 | Weiner |
| 2006/0212078 A1 | 9/2006 | Demarais et al. |
| 2006/0217772 A1 | 9/2006 | Libbus et al. |
| 2006/0217780 A1 | 9/2006 | Gliner et al. |
| 2006/0224188 A1 | 10/2006 | Libbus et al. |
| 2006/0224211 A1 | 10/2006 | Durand et al. |
| 2006/0229688 A1 | 10/2006 | McClure et al. |
| 2006/0235465 A1 | 10/2006 | Koo et al. |
| 2006/0235484 A1 | 10/2006 | Jaax et al. |
| 2006/0241716 A1 | 10/2006 | Finch et al. |
| 2006/0247719 A1 | 11/2006 | Maschino et al. |
| 2006/0247749 A1 | 11/2006 | Colvin |
| 2006/0259077 A1 | 11/2006 | Pardo et al. |
| 2006/0259090 A1 | 11/2006 | He et al. |
| 2007/0025608 A1 | 2/2007 | Armstrong |
| 2007/0027486 A1 | 2/2007 | Armstrong |
| 2012/0220363 A1 | 8/2012 | Bytnar et al. |

FOREIGN PATENT DOCUMENTS

| | | |
|---|---|---|
| DE | 10 2004 027 930 | 1/2006 |
| GB | 2 414 407 | 11/2005 |
| JP | 2006271689 | 10/2006 |
| JP | 2006280588 | 10/2006 |
| KR | 10 0197550 | 6/1999 |
| RU | 2181060 | 4/2002 |
| WO | WO 02/04068 | 1/2002 |
| WO | WO 03/092795 | 11/2003 |
| WO | WO 2005/007120 | 1/2005 |
| WO | WO 2005/014105 | 2/2005 |
| WO | WO 2005/079909 | 9/2005 |
| WO | WO 2005/087313 | 9/2005 |
| WO | WO 2005/105201 | 11/2005 |
| WO | WO 2005/123188 | 12/2005 |
| WO | WO 2006/014896 | 2/2006 |
| WO | WO 2006/021957 | 3/2006 |
| WO | WO 2006/054118 | 5/2006 |
| WO | WO 2006/070326 | 7/2006 |
| WO | WO 2006/084635 | 8/2006 |
| WO | WO 2006/089181 | 8/2006 |
| WO | WO 2006/101917 | 9/2006 |
| WO | WO 2006/108262 | 10/2006 |
| WO | WO 2006/108630 | 10/2006 |
| WO | WO 2007/089410 | 8/2007 |
| WO | WO 2008/088985 | 7/2008 |

OTHER PUBLICATIONS

Prizm Medical Inc., http://www.prizm-medical.com, prizm product: *Electro-Mesh TM Garment.*

Kraft et al, "Techniques to Improve Function of the Arm and Hand in Chronic Hemiplegia," *Arch Phys Med Rehabil.*, 1992, vol. 73, pp. 220-258.

Dimitijevic M.M. Mesh Glove. 1. "A Method for Whole-Hand Electrical Stimulation in Upper Motor Neuron Dysfunction," *Scand J. Rehabil Med.*, Dec. 1994; 26 (4): pp. 183-186.

Benzi et al., "Noise in Human Muscle Spindles," *Nature*, vol. 383, pp. 769-770, Oct. 31, 1996.

Wesenfeld et al., "Noise-Enhanced Tactile Sensation," *Scientific Correspondence, Nature*, vol. 383, p. 770, Oct. 31, 1996.

Glanz, "Sharpening the Senses with Neural Noise," *Science Magazine*, vol. 277, No. 5333, Issue of Sep. 1997, p. 1759.

Laskowski et al., "Refining Rehabilitation with Proprioception Training: Expediting Return to Play," *The Physician and Sportsmedicine*, vol. 25, No. 10, Oct. 1977.

Wong et al., "Rapid Dentritic Movements During Synapse Formation and Rearrangement," *Current Opinion in Neurobiology*, 2000, vol. 10, pp. 118-124.

(56) References Cited

OTHER PUBLICATIONS

McCall et al., "Muscle Afferent-Pituitary Axis: A Novel Pathway for Modulating the Secretion of a Pituitary Growth Factor," *Exercise and Sport Sciences Review*, vol. 29, No. 4, pp. 164-169, 2001.
Popovic et al., "Neurorehailitiaon of Upper Extremities in Humans with Sensory-Motor Impairments," *Neuromodulation*, 2002; 5 (1) pp. 54-67.
Shier, D., Butler, J., and Lewis, R., *Hole's Human Anatomy and Physiology* (Ninth Edition), McGraw-Hill 2002, pp. 456-457.
Kernan, Joe, "Gaming—Stroke Victims Playing to Recover," *Lifebeats Newspaper*, Oct. 18, 2007, pp. 5-6.
Written Opinion for PCT/US2008/050562, dated Aug. 11, 2008 (8 pages).
International Search Report for PCT/US2008/050562, dated Aug. 11, 2008 (4 pages).
International Preliminary Report on Patentability for PCT/US2008/050562, dated Jul. 14, 2009 (1 page).

\* cited by examiner

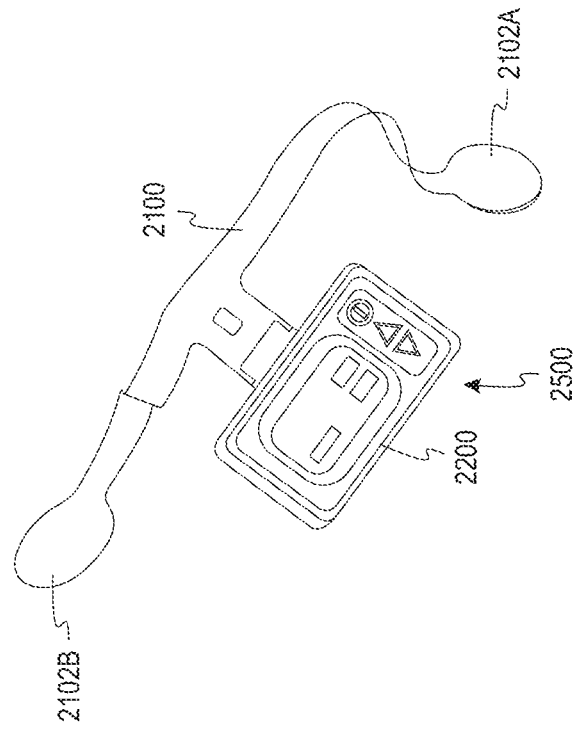
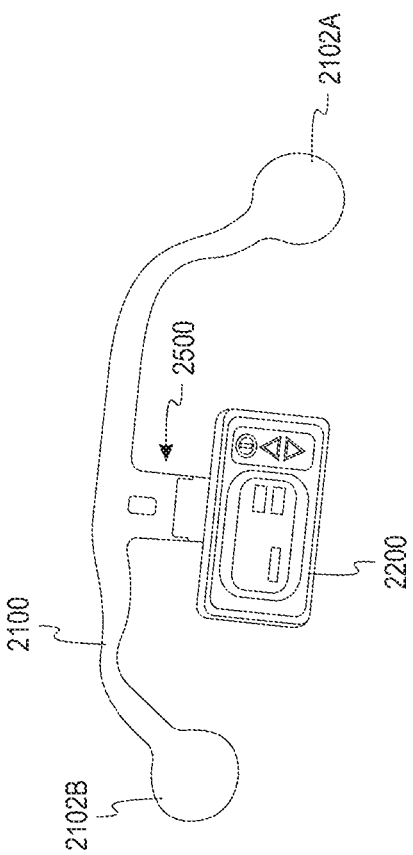
Fig. 13b
Fig. 13a

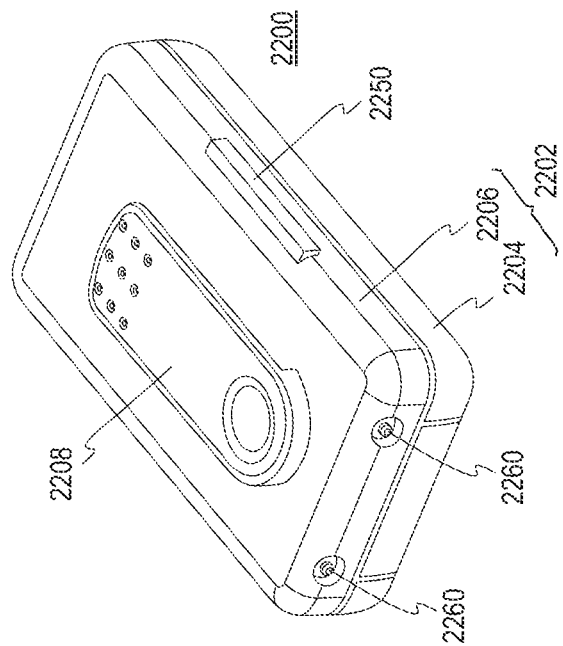
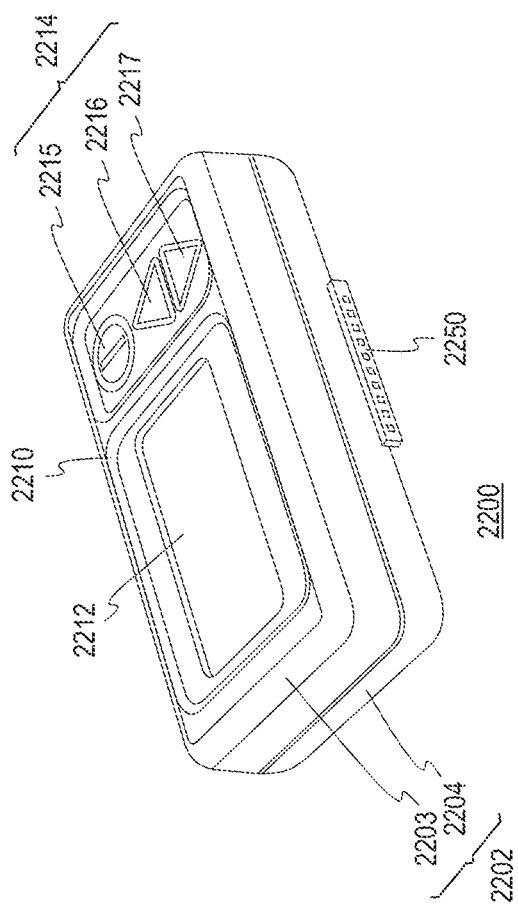
Fig. 15b
Fig. 15a

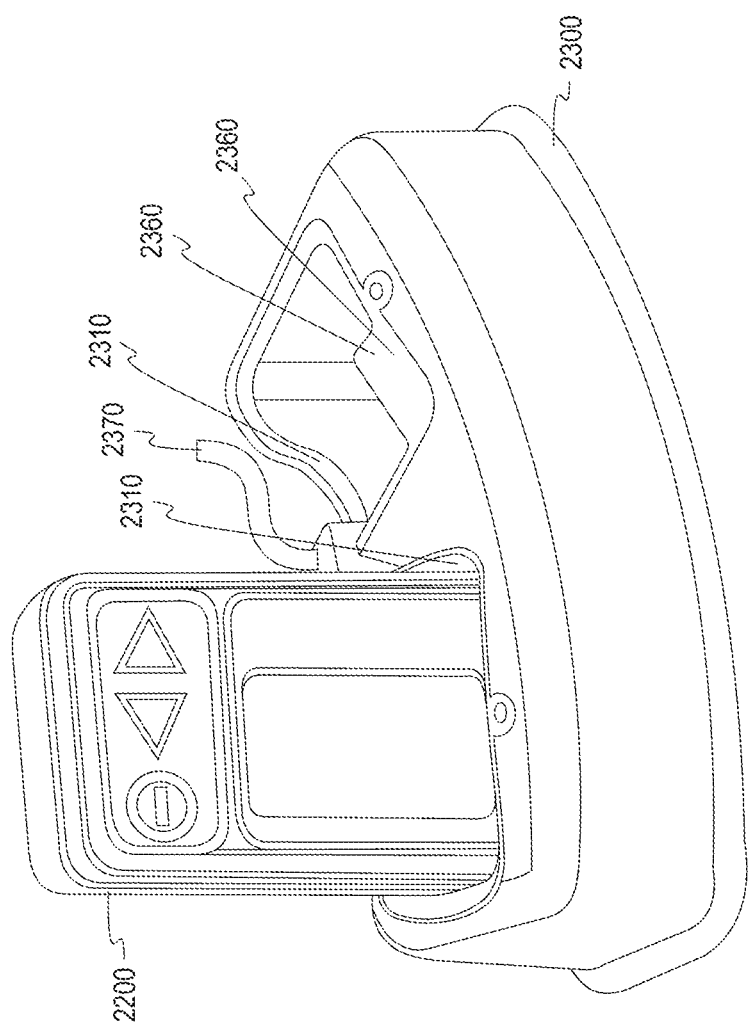

SYSTEM AND METHOD FOR NEURO-STIMULATION

CROSS REFERENCE TO RELATED APPLICATIONS

This application is a continuation of U.S. patent application Ser. No. 11/927,597, filed Oct. 29, 2007, which
(1) claims the benefit of and priority from U.S. Provisional Patent Application Ser. No. 60/880,026, filed Jan. 12, 2007; and
(2) is a continuation-in-part of U.S. patent application Ser. No. 10/429,252, filed May 5, 2003, now issued as U.S. Pat. No. 7,349,739, which claims the benefit of and priority from U.S. Provisional Patent Application Ser. No. 60/377,202, filed May 3, 2002;
each of which is incorporated herein in its entirety.

BACKGROUND OF INVENTION

Field of Invention

The present invention is generally directed to a system for providing neuro-stimulation, and more particularly, to a system that employs electrical current and/or mechanical vibration to deliver subthreshold and/or aperiodic stimulation to enhance detection and communication of sensory information.

Description of the Related Art

The nervous system of mammals is a complex set of interrelated and interacting sub-systems. The sub-systems are categorized and named both by their anatomic positions and by their function. At the highest level, the nervous system is divided into central and peripheral nervous systems. The central nervous system (CNS) is comprised of the brain and spinal cord; the peripheral nervous system (PNS) subsumes all the remaining neural structures found outside the CNS. The PNS is further divided functionally into the somatic (voluntary) and autonomic (involuntary) nervous systems. The PNS can also be described structurally as being comprised of afferent (sensory) nerves, which carry information toward the CNS, and efferent (motor) nerves, which carry commands away from the CNS.

Interconnections between afferent and efferent nerves are found in the spinal cord and brain. Taken together, certain groupings of afferent and efferent nerves constitute sensorimotor "loops" that are required to achieve coordinated movements in the face of perturbations from the environment and changes in volitional intent. In the periphery (trunk, upper extremities, and lower extremities), afferent nerves carry sensory information arising from special neurons that are sensitive to pain, temperature, and mechanical stimuli such as touch and vibration at the skin surface, and position, force, and stretch of deeper structures such as muscles, tendons, ligaments, and joint capsule. The term "proprioception" generally applies to sensory information directly relevant to limb position sense and muscle contraction. Combined with tactile (touch) sensation, mechanical sensory information is collectively known as "somatosensation."

Specialized "mechanoreceptor" neurons transduce mechanical stimuli from the body's interaction with the environment into electrical signals that can be transmitted and interpreted by the nervous system. Pacinian corpuscles in the skin fire in response to touch pressure. Muscle spindles, found interspersed in skeletal muscle tissue, report on the state of stretch of the surrounding muscle. Golgi tendon organs sense the level of force in the tendon. Free nerve endings in structures surrounding joints (ligaments, meniscus, etc.) provide additional information about joint position. Some of these mechanoreceptor systems are thought to interact directly via excitatory and inhibitory synapses and descending pathways to modulate the performance or interpretation of signals from other mechanoreceptor systems.

Sensory cells of all types are typically threshold-based units. That is, if the stimulus to a sensory cell is of insufficient magnitude, the cell will not activate and begin signaling. Such a stimulus is called "subthreshold." A stimulus that is above the threshold is called "suprathreshold."

Connections within the nervous system-brain, spinal cord, and peripheral nerves are highly changeable in the face of demands placed on the body. New forms of activity, pathologies, and injuries all can lead to durable changes, both beneficial and deleterious, in the nervous system. In healthy individuals, these neurological changes allow for the acquisition of new physical skills, a process termed "motor learning." Following certain types of soft tissue injury (e.g. rupture of the anterior cruciate ligament of the knee, a structure known to be rich in mechanoreceptors), and subsequent medical efforts such as surgery used to repair the damage, the nervous system can undergo compensatory changes to accommodate for loss of the natural sensory neurons. Similar PNS and CNS nervous system changes account for some individuals' ability to regain lost motor function following spinal or brain injuries. Taken together, these structural changes in the nervous systems—the creation of new useful interconnections or the pruning away of unused pathways—are termed "neuroplasticity" or "neuroplastic changes."

Recent research has established that afferent (sensory) activity from the periphery is one of the key drivers of neuroplastic changes in the nervous system, both in the PNS and CNS.

Stimulation below perception levels (i.e. subthreshold stimulation) used to enhance the function of sensory cells is described in U.S. Pat. Nos. 5,782,873 and 6,032,074 to Collins, the entire contents of which are incorporated by reference. Collins discloses a method and apparatus for improving the function of sensory cells by effectively lowering their threshold of firing. Briefly, a subthreshold stimulation, or subsensory stimulation or "bias signal," is input to the sensory neuron thereby predisposing the neuron to firing, without actually causing it to fire. In some embodiments, the stimulation may have an aperiodic waveform. In one particular embodiment, the bias signal is a broadband signal containing many frequencies, often termed "white noise." Since sensory cells are typically threshold-based units, lowering the sensory cell threshold decreases the level of outside stimulus needed to cause the sensory cell to respond (i.e. fire). Thus, the sensory cell, in the presence of the bias signal, is expected to respond to stimulus intensities that would normally be considered subthreshold to the neuron in the absence of noise. Both electrical and mechanical modalities of bias signal, used individually or in combination, may be used to effect the lowering of sensory neuron detection threshold. In other words, the stimulation essentially energizes sensory neurons based on a principle termed "stochastic resonance" (SR), so that they are predisposed to fire in response to stimuli from the environment. By increasing the sensitivity of mechanoreceptors, it is possible effectively to boost the flow of sensory information traveling from muscles, joints, and skin to the body's control centers in a fashion that is concordant with normal function.

One exemplary clinical use of increased sensory information is in the rehabilitation of individuals who suffer loss of sensorimotor function following stroke. According to the American Stroke Association, stroke is the leading cause of serious, long-term disability in the U.S., with the annual cost of stroke-related care expected to exceed $58 billion in 2006. Approximately 700,000 cases of stroke occur each year in the U.S. As a result, over 460,000 patients a year are left with motor impairments, the most common of which is hemiparesis, a weakness or partial paralysis of the body. In addition, a majority of the 5.5 million stroke survivors in the U.S. have some degree of impairment. While many patients improve with current physical rehabilitation therapy, most are left with significant motor deficits. Full recovery from stroke is uncommon. Thus, additional techniques for reversing the motor deficits caused by stroke are necessary. Boosting sensory traffic using the present invention is one such technique. A similar exemplary clinical use is physical rehabilitation for individuals who have suffered traumatic brain injury. Further exemplary clinical uses arise in treatment of individuals who have a temporary or permanent loss of sensory function resulting from aging, disease, or physical injury. For such individuals, the therapy is directed less toward driving neuroplastic changes and more toward providing an ongoing sensory boost as a palliative treatment for a chronic sensory condition.

SUMMARY OF THE INVENTION

Embodiments of the present invention provide neuro-stimulation systems that deliver stimulation to enhance the function of sensory cells. In view of the foregoing, an exemplary application applies a neuro-stimulation system to reverse the sensorimotor deficits caused by stroke. Focusing on mechanical sensory neurons in the periphery, embodiments of the present invention take advantage of the interplay between mechanoreceptors and neuromuscular performance. These sensory neurons provide touch, motion, and force feedback that is contributes to coordinated movement, acquisition of motor skills, and reestablishing sensorimotor function following injury. As such, embodiments of the present invention apply stimulation to mechanoreceptors to increase their ability to transmit sensory information. The mechanoreceptors receiving stimulation may include, for instance, subcutaneous mechanoreceptors as well as receptors in deeper structures. This stimulation enhances mechanical sensory information provided to the spinal cord and brain.

A neuro-stimulation system according to an exemplary embodiment may employ a controller which includes a user interface, a power supply, at least one electrical connector, and a processor with software. According to values entered into the user interface, the controller determines an electrical signal directed from the power supply to the electrical connector. The neuro-stimulation system also includes a stimulator detachably coupled to the controller via the electrical connector. The stimulator has a plurality of stimulating elements, including, optionally, at least one electrode device and/or at least one vibration element. The stimulator also includes an attachment element to attach the stimulator to a body part. The controller is operable, via the user interface, to drive at least one of the stimulating elements with an electrical signal, which in turn deliver electrical and/or mechanical stimulation to the body part. The vibration elements and/or electrodes may be driven to deliver stimulation that is subthreshold and/or stimulation that has an aperiodic waveform. In one particular embodiment, the stimulator is disposable and the processor determines usage of the stimulator and ensures that the stimulator is limited to a certain amount of use.

In an exemplary application, the neuro-stimulation system above is employed adjunctive to movement of a body part. For example, such movement may be employed as a part of post-stroke rehabilitative therapy. By applying stimulation from the neuro-stimulation system in proximity to the region of the body affected by stroke, the neuroplastic process (the creation of new sensorimotor pathways that allow healthy areas of the brain to assume the functions of the damaged portion) is enhanced. This therapy is particularly effective when used in conjunction with physical rehabilitation procedures. As such, preferred embodiments of the neuro-stimulation system may have small, lightweight components which facilitate the application of stimulation during physical therapy and do not interfere with the therapy with wires, connection cables, etc.

Other embodiments of the present invention may have other configurations and shapes for delivering controlled stimulation to any sensory cells of any body part according to a variety of therapeutic applications. Some embodiments may include only electrodes while others include only vibrating elements for delivering stimulation. For some applications, it may be preferable to include all components of a neuro-stimulation system in a single housing that is applied to the targeted body part. On the other hand, for other applications, it may be preferable to include the stimulator in an application body, i.e., a housing applied to the body part, while the controller has a separate housing which may be placed at a distance from the application body. Moreover, in other embodiments, a neuro-stimulation system may be incorporated within the structure of another distinct device, e.g., a wearable garment, where the application of stimulation improves an operator's ability to use the device or to enhance the effectiveness of the device. In yet other embodiments, stimulator elements (whether strictly electrical, mechanical, or both) may be implanted under the skin of the subject. The controller that is attached to the implanted stimulator elements may itself also be implanted, with connecting means traversing under the skin to the stimulator elements. In addition, the controller may remain extracorporeal with connecting means passing through the skin to the implanted stimulator elements.

Still other aspects, features, and advantages of the present invention are readily apparent from the following detailed description, by illustrating a number of exemplary embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE FIGURES

FIG. 13A illustrates the exemplary neuro-stimulation system of FIG. 10A secured to a subject's arm for use during post-stroke rehabilitative therapy.

FIG. 13B further illustrates the exemplary neuro-stimulation system of FIG. 10A secured to a subject's arm for use during post-stroke rehabilitative therapy.

FIG. 15A illustrates the controller of the exemplary neuro-stimulation system of FIG. 10A.

FIG. 15B further illustrates the controller of the exemplary neuro-stimulation system of FIG. 10A.

FIG. 19 illustrates a recharging base for the exemplary neuro-stimulation system of FIG. 10A.

DETAILED DESCRIPTION

Figure 1:
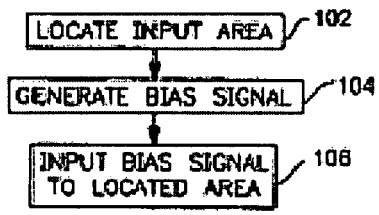
FIG. 1 is a flow chart of a method for enhancing the function of a sensory cell.

Throughout this specification and the drawing figures associated with this specification, numerical labels of previously shown or discussed features may be reused in another drawing figure to indicate similar features.

The preferred embodiments of the present invention provide a method and system for improving sensorimotor performance of humans, non-human mammals, and non-mammalian animals, hereinafter termed "subjects." Improvements in sensorimotor performance are meant to include immediate, i.e., acute, effects, such as improved dynamic joint stability, and more durable effects as would result from neuroplastic changes in the PNS or CNS. The method comprises inputting a bias signal to sensory cells of the subject, so as to improve the function of those sensory cells by effectively lowering their threshold of firing, while the subject engages in physical activity. Such physical activity may or may not be specifically pre-defined depending upon the desired outcome. Acting in conjunction with this preferred method is a preferred apparatus that comprises a wearable device and other electromechanical components that provide a convenient and secure means of delivering the bias signal to the subject. As used herein, the term "bias signal" will be taken to mean a subthreshold form of stimulation to a sensory neuron, whether electrical or mechanical in nature, whose waveform may be periodic, aperiodic, deterministic, or non-deterministic and may contain one or many frequencies.

The method and system according to the preferred embodiments of the present invention are useful, for example, to enhance sensorimotor function in healthy individuals as well as in individuals with disorders, diseases and/or injuries. For example, the method and system could be used by healthy individuals striving to learn a new motor skill, such as might be required for athletic activity. In another example, the method and system could be applied to individuals with elevated sensory thresholds or other neurological dysfunction, such as might arise from aging, peripheral neuropathies, or strokes.

FIG. 1 is a flow chart of a method for enhancing the function of a sensory neuron according to one embodiment of the present invention. In step 102, an area associated with the sensory cell whose function is to be enhanced and to which a bias signal is to be input is located. The located area is hereinafter referred to as the input area. Once the input area has been located, the bias signal is generated in step 104. Then in step 106, the bias signal is input to the input area so as to effectively lower the threshold of sensory cells with which the input area is associated.

Figure 2:
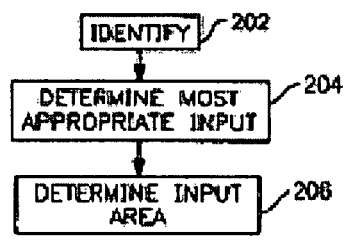
FIG. 2 is a flow chart of a method of locating an input area.

FIG. 2 is a flow chart showing one embodiment of locating an input area according to step 102. Locating the input area depends, inter alia, on the sensory system whose function is to be improved and the method by which a bias signal may be input to sensory cells associated with the sensory system. Step 202 is a preliminary step in which an identification scheme is undertaken to identify a particular sensory system whose function is to be enhanced. The identification scheme, to some extent, depends on the cooperation of the individual. That is, this step is similar to a diagnosis, however, the individual need not be suffering from any disease or disorder to be subject to the enhancement process contemplated herein. In one embodiment, the sensory system whose function is to be enhanced is one whose function has been degraded by disease.

In an alternative embodiment, the sensory system to be enhanced is one that functions normally. In step 204, the most appropriate way of inputting a bias signal to the target sensory system is determined. The most appropriate input means depends on a number of factors including, the target sensory system, the nature of the transduction system for the target sensory system, the present state of the target sensory system (i.e., whether it is impaired or in any way dysfunctional), and the nature of the signal which is to be determined (e.g., the amplitude and frequency content of the signal). Input means that are appropriate in certain circumstances include, but are by no means limited to, nerve cuffs, implanted electrodes, surface electrodes, muscle stimulators, tendon stimulators and magnetic field stimulators.

Once the most appropriate input means is determined in step 204, the input area is determined in step 206. The location of an input area depends on the same factors as the determination of the most appropriate input means. The location of the input area, however, varies for a particular input means depending on, among other factors, whether the target sensory system is in any way dysfunctional, the cause and location of any such dysfunctionality, and the nature of the stimulator to be used. More specifically, if a dysfunctionality caused by some physical damage to sensory cells is present in the sensory system, it may be necessary to locate the input area such that the bias signal will bypass the physical damage causing the dysfunctionality. Further, the fact that some stimulators, e.g. implanted electrodes or vibratory elements, may require invasive procedures while others, e.g., surface electrodes or vibratory elements, require only noninvasive procedures is also a factor to consider.

Figure 3:
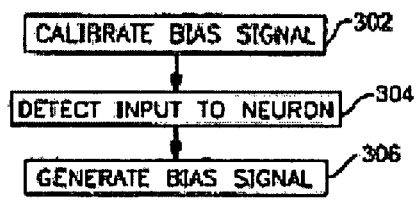
FIG. 3 is a flow chart of a method of generating a bias signal.

Once the input area is determined and the input means installed, the bias signal to be input is generated. FIG. 3 shows one embodiment of a method of generating a bias signal. In an initial step 302, the bias signal is calibrated. That is, an optimal level for the bias signal is determined. Depending on the determinations of steps 204 and 206, there exists a particular form of bias signal for which the signal detection ability of a given neuron in the target sensory system is optimally enhanced. For example, a bias signal having parameters with certain predetermined values will give rise to optimal enhancement. Calibration helps to ensure that certain parameters of the bias signals generated will be adjusted to achieve optimal enhancement. Examples of signal parameters of the bias signal that may be calibrated are amplitude (whether measured as peak-to-peak, RMS, or some other method), frequency or frequency content (as determined perhaps by signal spectrum analysis), offset (D.C. bias), intensity, and variance (e.g. the computed time-based standard deviation in signal amplitude). Calibration is typically accomplished prior to installation of the enhancement system and may be accomplished intermittently while the enhancement system is installed. If calibration is to take place while the enhancement system is installed, then it is desirable to install the enhancement system so it is accessible from the outside of the body so that calibration may be accomplished noninvasively.

In one embodiment, the calibration is accomplished by inputting an input signal of interest to a sensory cell coupled with a bias signal produced by the enhancement system. The response of the sensory cell to the combined input is recorded as a function of a parameter of interest in the bias signal. That is, the response of the sensory cell is recorded as a parameter of interest in the bias signal is modulated. Using the recorded results, the coherence between the combined input and the response of the sensory cell is then characterized by computing some measure such as the cross-correlation coefficient described below. The response of the sensory cell is maximally enhanced when the coherence measure is maximized. This maximally enhanced response corresponds to some value or range of values of the bias signal parameter of interest that can be determined by, for example, examining a record of the bias signal. Thus, an optimal value or range of values for the parameter of interest of the bias signal is determined. The process can be repeated using other input signals and parameters of interest thereby determining a bias signal with optimal parameters for input signals with varying parameters.

According to one embodiment of the present invention, the bias signal is optimized by examining the cross-correlation coefficient, $C_1$:

$$C_1 = \frac{C_0}{\sqrt{\overline{S^2(t)}} \sqrt{\overline{(R(t) - \overline{R(t)})^2}}}$$

where $$C_0 = \overline{S(t)R(t)}$$

where S(t) is the input signal, R(t) is the output of the sensory neuron or sensory system (e.g., the neural mean firing rate signal or the neural spike train), and the overbar denotes an average over time. S(t) and R(t) can be measured with any appropriate transducers, for example, a needle electrode may be used to measure the output of a neuron. Maximizing $C_1$ corresponds to maximizing the coherence between the input signal S(t) and the neuron's output R(t). The value of $C_1$ for a given input signal will depend upon the parameter of interest of the bias signal. Thus, a bias signal having parameters which will produce the desired output R(t) may be determined.

The results of the calibration process may be utilized, for example, by modulating the bias signal in response to an input signal or by determining a set of parameter values which, on average, will achieve optimal enhancement for any input signal. In the first instance, parameter values for the bias signal are, for example, tabulated against parameters of the input signal. Upon occurrence of an input signal, certain parameters of the input signal are measured, and a bias signal having corresponding parameter values is generated by, for example, referencing the tabulated results. In this way, the bias signal is modulated or optimized for each particular input signal. In the second instance, a single set of parameter values which will achieve optimal enhancement for most signals is calculated and used to generate a bias signal which is for use in response to every input.

After the input device has been calibrated and installed, in one embodiment, an input signal to the neuron is detected. As will be explained in conjunction with FIG. 4, one embodiment of a system for enhancing the function of a sensory neuron includes signal detection capabilities, for example, a transducer and signal processor. Thus, in step 304, input signals to the neuron are detected using the signal detection capabilities.

Once an input signal is detected in step 304, a bias signal is generated in step 306. As explained above with respect to the calibration process, the bias signal has either parameters which are modulated depending on certain parameters of each input signal or a constant, non-modulated, set of parameters which are designed to optimally enhance the function of a sensory cell in response to most input signals. If a bias signal having a non-modulated set of parameters is used, then a somewhat simpler input system is used. In general, the nature of the bias signal to be used, that is, modulated or non-modulated, depends on the nature of the sensory system to be enhanced. Once the bias signal is generated, it is input to the neuron in step 106.

In the embodiments described above, a bias signal is produced only in response to the detection of an input signal to the neuron. In an alternative embodiment, after the input device has been calibrated and installed, a bias signal is continuously generated and input to the neuron. That is, an input signal does not need to be detected. In a method according to this embodiment, the bias signal is either modulated or non-modulated. If the bias signal is modulated, then the continuously generated bias signal is modulated as described above, when an input signal is detected. If a non-modulated bias signal is used in this embodiment, then a simplified input system may be used. As discussed above, whether a modulated or non-modulated bias signal is used depends upon, inter alia, the nature of the system to be enhanced.

In another embodiment, a distributed enhancement process is used. In this embodiment, the enhancement process described above is modified such that a bias signal is generated and input to neurons at a plurality of locations to stimulate an array of sensory cells and thereby provide a distributed enhancement effect. In this distributed enhancement system, as above, either a continuous or non-continuous, and modulated or non-modulated bias signals may be used. As one example, if the sensory function of the urinary tract is to be enhanced, a bias signal may be input to a number of distributed points around the bladder so that improved fullness sensation is obtained.

Figure 4:
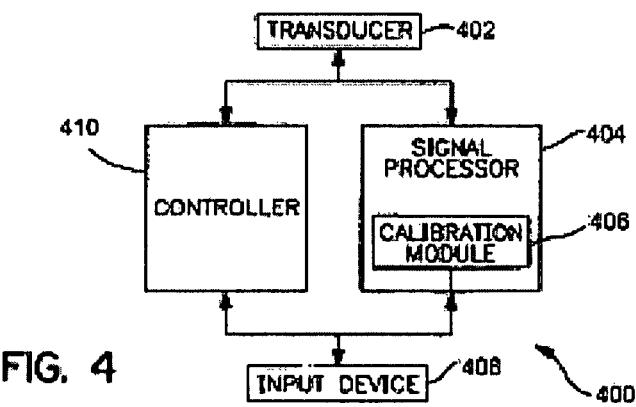
FIG. 4 is a schematic depiction of a system for enhancing the function of a sensory cell.

One embodiment of an enhancement system 400 for implementing the method for enhancing the function of a sensory neuron is shown in FIG. 4. Enhancement system 400 comprises a transducer 402, a signal processor 404, an input device 408 and a controller 410. Enhancement system 400 operates on electrical signals. An input signal to a sensory cell is typically initiated by contact with the outside world which contact is generally not in the form of an electrical signal. An input signal might be initiated by, for example, a touch, a movement of a body segment, a sound wave or light. One function of transducer 402 is to detect input signal initiating contacts and convey the contact to enhancement system 400 generally and signal processor 404 specifically. Another function of transducer 402 is to convert an input signal initiating contact into a signal in a form that is usable by enhancement system 400. The mechanism used for transducer 402 depends on the sensory system targeted. As an example, if the auditory system is being targeted for enhancement, transducer 402 may take the form of a stimulating electrode or an array of stimulating electrodes arranged in the vicinity of the ear. As another example, if the proprioceptive system is being targeted for enhancement, transducer 402 is a tendon stimulator, implemented by way of a piezoelectric transducer, installed or attached via elastic straps to a tendon or parent muscle associated with the sensory cells whose function is to be enhanced. As still another example, if the vibration or touch-pressure sensation system is being targeted for enhancement, transducer 402 is a surface electrode installed or applied over the skin of the area of the body containing the cells to be stimulated. Such an electrode is attached using flexible electrode/skin interfaces.

Signal processor 404 produces a bias signal to be input to the sensory system targeted for enhancement through input device 408. Signal processor 404 is electrically connected to transducer 402, input device 408 and controller 410. As discussed above, a bias signal may be either continuous or non-continuous and modulated or non-modulated. The form of signal processor 404 depends upon the desired form of the bias signal to be produced. In one embodiment, where a non-continuous, modulated bias signal is desired, signal processor 404 preferably includes both signal detection capabilities and look-up table capabilities to store parameter values for the bias signal. In another embodiment, where a constant, non-modulated bias signal is desired, signal processor 404 does not necessarily require signal detection capabilities and look-up table capabilities. In one embodiment, signal processor 404 is either a special function IC or a general micro-processor and is preferably small, lightweight and portable. Further, signal processor 404 preferably includes signal conditioning and data acquisition abilities. In one embodiment, a PCMCIA chip or card is used as signal processor 404.

Signal processor 404 also includes calibration module 406. Calibration module 406 enables adjustment of the bias signal produced by signal processor 404. For example, for optimal enhancement, signal processor 404 produces a bias signal having predetermined parameters (for example, a predetermined amplitude and frequency) in response to a particular signal received from transducer 402. If these predetermined parameters of bias signal are not properly adjusted, the bias signal will not optimally enhance the function of the targeted sensory system. Calibration module 406 enables these predetermined parameters to be adjusted so that an optimal bias signal is produced. Calibration is typically accomplished prior to installation of enhancement system 400 and may be accomplished intermittently while enhancement system 400 is installed. If calibration is to take place while enhancement system 400 is installed, then it is desirable to install signal processor 404 so it is accessible from the outside of the body so that calibration may be accomplished noninvasively. In an alternative embodiment, signal processor 404 is provided with remote access capability enabling calibration to take place noninvasively whether or not signal processor is accessible from outside of the body.

Input device 408 conveys the bias signal produced by signal processor 404 to the targeted sensory system. Depending on what the targeted sensory system is, input device 408 might take a number of different forms as discussed above. Input devices that are appropriate in certain circumstances include, nerve cuffs, implanted electrodes, surface electrodes, muscle stimulators, tendon stimulators, and magnetic field stimulators. The manner in which input device 408 conveys the bias signal to the targeted sensory system depends on the form of input device 408 and the targeted sensory system. For example, a nerve cuff or implanted electrode is suitable for use when the urinary tract is the targeted sensory system and is typically implanted surgically and conveys the bias signal to the sensory components of the system. A muscle or tendon stimulator, on the other hand, is more suited to mechanically stimulate the proprioceptive system. Such a stimulator mechanically stimulates the proprioceptive system by vibrating a muscle or tendon associated with that system, for example a muscle in the vicinity of a joint. Muscle or tendon stimulators can be applied noninvasively using, for example, an elastic band. In one embodiment, where the targeted sensory system is the vibration or touch-pressure sensation system, a surface electrode-based system is used as input device 408. Specifically, the glove electrode, the sock electrode, and the sleeve electrode, sold under the name ELECTRO-MESH™ may be used as input device 408. The surface electrode system is placed over the body part of interest, e.g., the hand or foot. Still further, input device 408 may be a magnetic field stimulator used either noninvasively or invasively. For example, a magnetic field stimulator may be used to stimulate cutaneous sensory neurons by positioning the stimulator on the exterior of the body in the vicinity of the sensory cells to be stimulated using elastic bands. A magnetic field stimulator may be used invasively, for example, by surgically implanting the stimulator to stimulate sensory neurons in the area of the bladder.

Controller 410 controls interaction between transducer 402, signal processor 404 and input device 408. The implementation for controller 410 depends upon, among other things, the form of bias signal desired. That is, where a non-continuous, modulated bias signal is desired, controller 410 may be implemented using a microprocessor. In a simpler embodiment, where a continuous, non-modulated bias signal is desired, controller 410 may be implemented using a switch that simply activates the enhancement signal. Alternatively, signal processor 404 may be adequate, so that controller 410 is unnecessary for such an embodiment. By way of example only, controller 410 comprises a microprocessor with suitable programming, or any digital controller. In one embodiment, controller 410 is implemented with the aforementioned PCMCIA chip or card.

The nature and amplitude of the bias signal is controlled in accordance with the type of sensory cell to which the bias signals are applied. Repetitive waveform, pulse or DC signals of the type typically used for other types of injury treatment (e.g. pain suppression, bone healing) are often be avoided in the practice of the present invention, as sensory cells can adapt to simple deterministic signals thereby reducing or eliminating over time the effect of such signals on the sensory cells. Instead, in accordance with the invention, non-deterministic noise signals, such as random, aperiodic noise signals, or recorded repetitions of noise signals are preferably used, so that the sensory cells do not adapt to the noise signals over the extended period of noise signal application that occurs during a physical training regimen. These signals can be continuously generated signals such as those created by known instruments, including a computer random number generator, a noise diode, or thermal noise from a resistor or other electrical component. Sampled signals, such as signals stored in a storage device (RAM, ROM, etc.), or periodically recorded noisy signals, may also be employed.

The sensory cell areas containing neurons to be affected by bias signals may be found at different depths in the human body, causing different signal transmission filtering characteristics to exist between certain of the sensory cells and the signal input device. In a preferred embodiment, the bias signal can be combined with other signal types to overcome this problem. For example, a chirped signal can be formed by overlaying a noise signal with a swept frequency signal that regularly sweeps through a signal frequency range. This combined signal may be tailored to permit the amplification of frequency ranges that are normally attenuated by transmission in the body. Thus, the signal is compensated at the skin-surface level for expected attenuations that would occur prior to it reaching the target sensory cell. This technique might also be used to reduce the effort required to determine an efficacious signal since it might contain all desired frequency ranges.

Another method of the present invention involves enhancing various neurophysiologic functions by applying an externally produced bias signal to a sensory cell area, as described above, while the subject is performing a predefined physical activity. Neurophysiologic functions enhanced by this method of the present invention include, for example, limb position sense enhancement, increase release of growth hormones, enhanced peripheral neuroplastic changes, and enhanced central, including cortical, neuroplastic changes.

Most physical training regimens are undertaken to induce, among other things, motor learning, i.e. the acquisition of new motor skills or the regaining of motor skills that have been lost due to injury or disease. To achieve the aforementioned sensorimotor performance enhancements, while a subject performs a specified physical activity bias signals are applied to sensory cells involved in the specific physical activity to lower the threshold at which such cells are triggered by the external stimuli resulting from the activity. By making the sensory cells more responsive, the number of action potentials produced for any given amount of external stimuli is increased, thereby improving the rate and/or quality of motor learning resulting from the activity.

Coordinated motion of the extremities, for example, requires precise interplay between descending volitional signals from the brain, muscle contraction, limb movement, and interaction with the environment. This tight control is reliant, in part, on sensory feedback of a mechanical nature from the extremities involved in the motion. Somatosensory information, e.g. tactile information from foot sole and proprioceptive information from knee joint, is clearly important both to normal gait and to more vigorous activities such as jumping and landing. The method of the present invention is effective to boost coordinated sensory information from the mechanoreceptors involved in limb position sense during movement of the extremities. This added information content during movement provides a means for improved sensorimotor control. Such improvements result in enhanced balance, corrected gait patterns, and prevention of injuries by avoiding, for example, hyperextension of joints.

In one embodiment of the invention, a bias signal is provided during a training regimen to a plurality of structures that participate in stability of a joint in a subject, to thereby promote joint sensation and feedback to enhance stability in the subject. For example, at least one input device, e.g. an electrode, can be placed at or near the articular space such that sensory cells in or adjacent to the ligaments, the joint capsule and meniscus, are stimulated. The bias signal is provided at a level below the perception threshold of the sensory cells associated with the structures as well as below the cutaneous pain threshold.

In another preferred embodiment, the bias signal can be provided to at least two structures that maintain joint stability and are on opposite sides of the joint such that the performance of the sensory cells contained in these structures are enhanced. Preferably, a bias signal is provided at or adjacent to the joint and at least two different antagonist muscles on opposite sides of a joint where the action of these muscles determines the relative flexion and extension of the joint.

The bias signal can be provided simultaneously to each of the structures or it can occur sporadically at each of the structures. Preferably, the bias signal is repeatedly provided to each of the structures, e.g., the bias signal is repeated such that the bias signal is simultaneously provided to each of the structures or the bias signal is repeated such that the bias signal is sporadically provided to each of the structures a plurality of times.

Specific bias signal ranges are applicable to specific types of bias signals used in accordance with this invention. For example, electrical signals are preferably applied within a current density range of about 1 $\mu A/in^2$ to about 1000 $\mu A/in^2$ and a frequency range of about 0 Hz to about 10,000 Hz the skin surface of a recipient. Mechanical signals preferably have a displacement at the skin surface within the range of about 1 $\mu m$ to about 10 mm and frequencies within the range of about 0 Hz to about 1000 Hz. Mechanical signals can be remotely controlled by providing mechanical actuators on the skin surface that receive remotely generated waveform signals from a remote transmitter and convert these signals to mechanical signals. In wireless systems, electrical signals can also be transmitted from a remote transmitter to electrodes that apply electrical signals to a subject. All bias signals are preferably designed to allow for complex constructive and/or destructive patterns.

Naturally-occurring growth hormones, as another example, are released in humans by the pituitary gland. These hormones are part of the body's system of changing the architecture of muscle and bone in response to changes in activity. For example, increases in muscle bulk in response to exercise are partly caused by increased amounts of circulating growth hormone in the body. Recent research has established that afferent signals from the periphery, specifically those arising from muscle, spur release of specific types of growth hormone from the pituitary (McCall, et al., 2000). In accordance with the present invention, sensory feedback neurons are made more active by applying bias signals to lower the sensory cell threshold during a physical training regimen. For example, sensory information from muscle spindles that boost release of growth hormone in response to activity is increased. This is especially beneficial to individuals, e.g. strength trainers, working to regain muscle bulk and bone integrity following trauma or prolonged periods of inactivity. In some cases, the increase in growth hormone release may be sufficient to eliminate the need for growth hormone replacement therapies and the need for growth hormone supplements.

Interconnections and efficiency of sensorimotor pathways in the periphery are a manifestation of the acquisition of new motor skills. That is, a key result of training and practice is the creation of these new pathways. Indeed, even increases in strength are due as much to neurologic changes as to increases in muscle mass, especially early in strength building regimens. Recent research has shown that afferent activity spurs the creation of new synapses ("synaptogenesis"), one of the underlying neurophysiologic processes of peripheral neuroplasticity (Wong, et al., 2000). Applying bias signals to an input area in accordance with the method of the present invention increases information-rich sensory traffic from the periphery drives neuroplastic changes in the periphery. A common perception of strength training is that it involves only muscularity, and that neurology is not a consideration. In actuality, neurological factors are central to the development and maintenance of muscular strength. In the initial stages of a strength training regimen, muscle mass does not increase significantly but strength does as a result of the neuromuscular learning process. By applying bias signals to an input area in accordance with the method of the present invention, the time for completing this process is significantly reduced by lowering the threshold for the sensory cells involved during this stage of the strength training. As a result, information-rich traffic from the periphery drives neuroplastic changes in the periphery that, among other things, increases the rate by which muscle mass formed.

Strength training performed in accordance with the present invention is also effective in enhancing crossover strength changes in human appendages such as the arms or the legs. Strength training research has shown that when only one appendage is subjected to a strength training regimen, the strength of the untrained appendage increases to some degree. Thus, if one appendage is immobilized by a cast or brace, the strength of the immobilized appendage can be enhanced by using the method of the present invention to lower the sensory cell thresholds in the opposite appendage during a strength training regimen for the opposite appendage.

Many athletic training programs are directed to the improvement of balance that is required when weight is rapidly transferred from side to side. Balance enhancement training regimens have included prolonged repetitive side-to-side motion to promote motor learning that results in enhanced balance. Again, in combination with this side-to-side training regimen, the present invention involves lowering affected sensory cell thresholds during the training to achieve with greater rapidity enhanced balance.

Moreover, both normal acquisition of new motor skills, and the process of regaining motor skills following injuries such as stroke, rely on the elimination and creation of new connections throughout the sensory and motor cortices. Recent research has established that sensory activity from the periphery is one of the underlying drivers of these beneficial neuroplastic changes in the brain (McKay, et al., 2002). Applying a bias signal to an input area in accordance with the method of the present invention also increases afferent traffic thereby accelerating the improvement of motor skills.

Figure 5B:
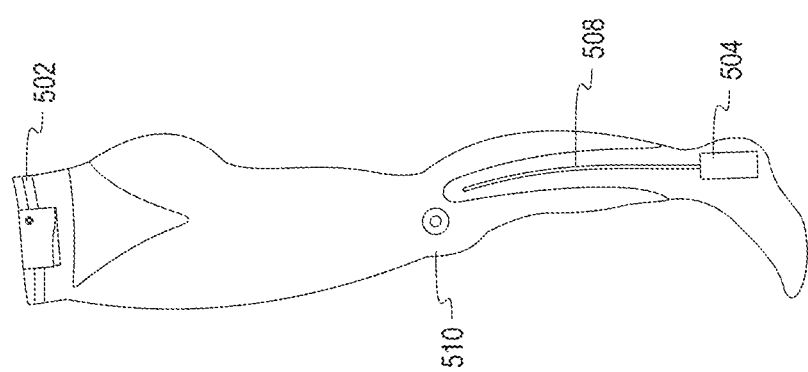
FIGS. 5A-5B illustrates an system for enhancing sensorimotor performance.
Figure 5A:
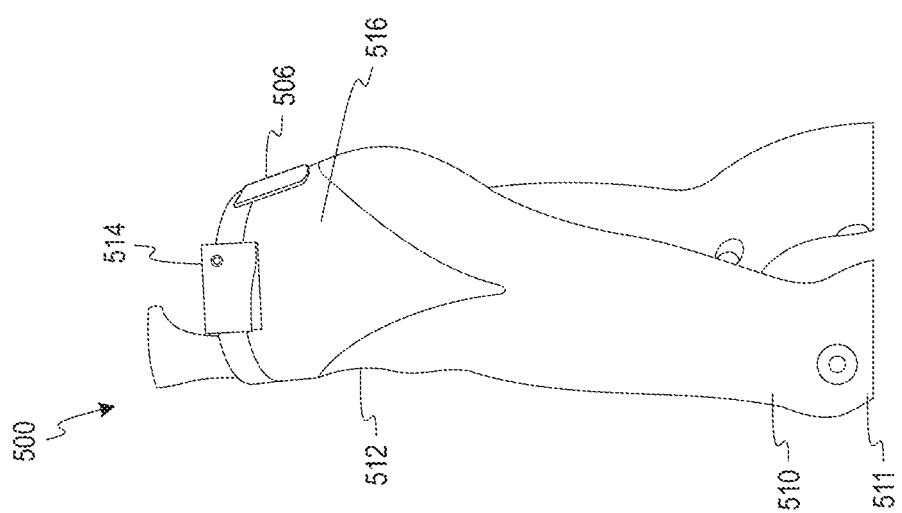

FIGS. 5A-5C, illustrate one preferred system for applying input signals in accordance with the method of the present invention as applied during a physical training regimen. The system comprises a lower extremity garment 500 that extends from the waist of a user down both legs. A belt 502 secures the garment at the waist while foot straps 504 which extend beneath the user's feet hold the garment snugly against the body during lower body motion. Foot straps are preferably composed of neoprene or other known elastic material. Garment 500 preferably includes a plurality of belt straps 506 positioned circumferentially around the waist section of the garment 500. The loose ends of straps 506 fold over belt 502 and attach to garment 500 via Velcro or other known fastening means to, in effect, form a belt-loop that securely retains belt 502 at waist level.

Garment 500 is designed for the application of input signals at and below the knee. Consequently, the legs of the garment have closures 508 that permit input device 510 to be positioned at selected positions relative to the knee, calf and/or lower leg muscles while also being maintained in place to garment 500. External caps 511 clip through the garment and onto input device 510, so as to securely hold input device 510 in place. Signal input devices 510, therefore, can be placed at virtually any position on the garment as necessary for various applications and to accommodate the anatomy of the subject. To fit garment 500 to a user, input devices 510 are first placed on the skin of a user relative to specific muscles, joints, etc. Garment 500 is then carefully donned over input devices 510 and external caps 511 are clipped through garment 500 to hold input devices 510 in place. Garment 500 is preferably formed of neoprene or any known stretchable material that enables the garment to closely conform to the subject and securely hold the input devices 510 securely against the subject's skin to prevent displacement of the input devices 510 during the prolonged motion involved in an exercise regimen.

Cables 512 electrically connect the input devices 510 to a signal generator 514. Signal generator 514 provides power to input device 510 on the inner surface of the garment so that changes in the position of the electrodes can be adjusted within the area of input devices 510. Cables 512 are preferably secured to garment 500 such that there are no loose cables to impede body movement. In a preferred embodiment, cables 512 extending from signal generator 514 are secured within side pockets 516 of garment 500. Cables 512 extend through pockets 516 into a conduit 520 that extends downward along the leg portions of garment 500. Conduit 520 branches into multiple conduits at knee level, so as to accommodate input devices 510 positioned at various positions on and about the lower leg. Input devices 510 can be attached at any position along the length of cables 512. A cable guide 522 made of plastic or similar material surround conduit 520 so as to maintain the opening of conduit 520 into pocket 516. The conduit opening maintained by cable guide 522 allows cable 512 to be fed into and out of the length of conduit 520 with considerable ease.

Cable 512 is preferably of sufficient length to permit controller 514 to slide from the side of belt 502 to the back of the belt 502. Thus, signal generator 514 can be repositioned at various positions along belt 502, so as not to restrict movement required by specific exercises. Signal generator 514 can also be worn at other locations or hand held. Generally, the placement of signal generator 514 is determined based upon location of the joint to be stabilized, the comfort of the subject and/or the ease of motion by the subject. To eliminate cables 512, signal generator 514 may include one or more wireless transmitters operative to transmit signals to signal generator 514 and/or input devices 510.

Figure 6:
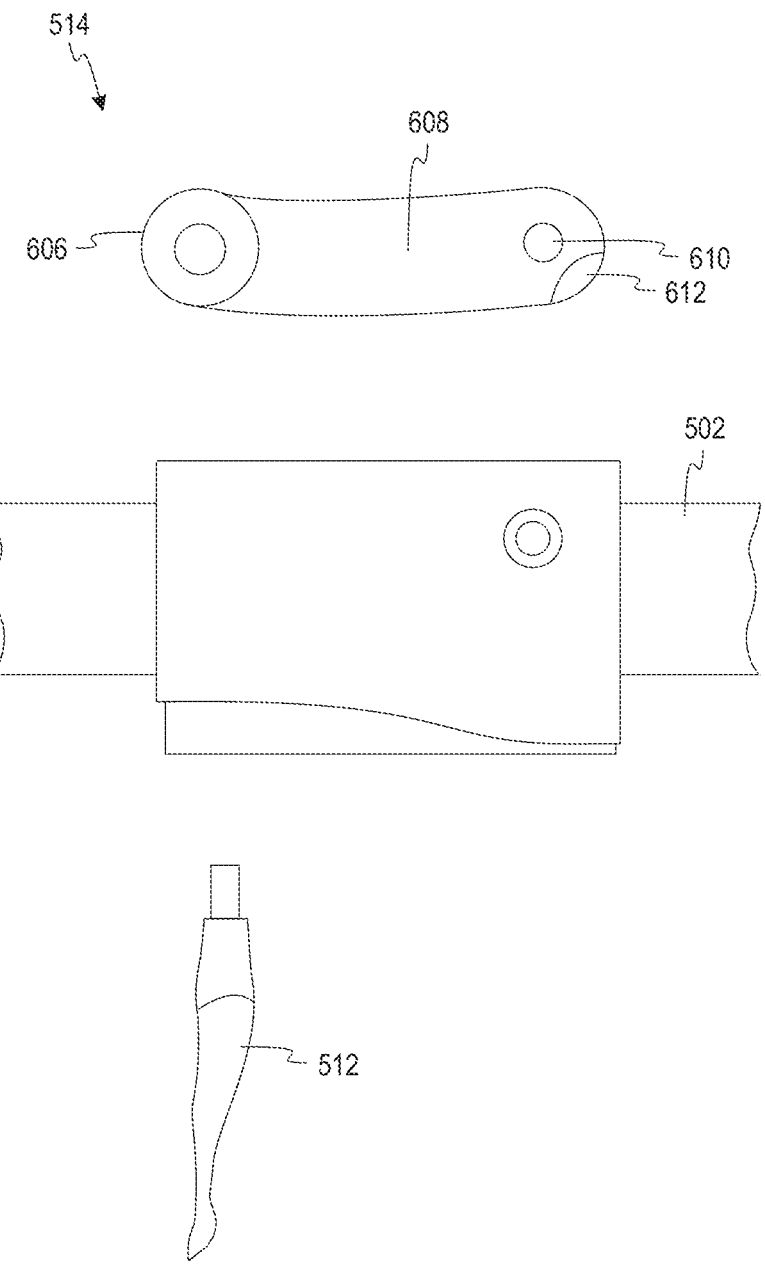
FIG. 6 is illustrates a signal generator of the present invention.

Signal generator 514, as shown in FIG. 6, includes a signal processor 404, a controller 410, control dials 606, a display 608, a test button 610, and an infrared port 612. Display 608 shows graphic information that is of interest to the user or clinician such as current stimulation program, remaining battery life, stimulation levels, active channels, errors etc. Infrared port 612 (or wireless or cabled, etc.) provides a link to a computer station that permits the downloading of custom stimulation patterns and waveforms. Test button 610 permits the confirmation of appropriate controller function. Controls dials 606 are operative to vary the amplitude of the noise signals provided to the signal input devices 510 so as to maintain the signals below the threshold level of the sensory cells targeted, as well as below the subcutaneous threshold level. The electrical current density at each signal input device 510 is determined by the current amplitude and the size of the electrode. The current density must be maintained within an acceptable range. In the case of electrical stimulation, channels may be electrically isolated from one another or may share a common ground.

Input devices 510 can apply, through the skin, input signals to the structure associated with joint orientation. As earlier noted, the input devices 510 in the garment can be surface electrodes, muscle stimulators, tendon stimulators, and magnetic field stimulators, vibratory stimulators, e.g. small electromagnetic rotary motors or flat motors (i.e. pancake motors), piezoelectric actuators, ferrofluid magnetic actuators, or electrorheologic actuators, or other known signal input device The signal input devices are appropriately sized and arranged to localize stimulation to a desired structure. For example, knee electrodes and actuators are sized as to not impede or restrict motion and to limit (target) the stimulation to the sensory neurons of interest. Signal generator 514 can be programmed to vary the intensity and timing of the signals. For example, when more than one input device 510 is used, the location and polarity of the signals can be varied. Similarly, the stimulation can simultaneously occur at each of input devices 510, or the stimulation can occur sporadically between each of input devices 510. The power and frequency of stimulation can also be controlled. The signal is at a level below the perception threshold of sensory cells associated with the various structures that play a role in the joint's stability. Thus, the signal is at a level below that required to trigger the sensory cells in those structures.

The level of the signal supplied by signal generator 514 may also be enough to stimulate other cells that are located in structures not directly involved in joint stability. For example, sensory cells within the skin may perceive a signal supplied through an input device 510 placed upon the skin, but the level is still below the threshold required to stimulate the sensory cells of the structure, e.g., such as the hamstring below the skin, which is associated with the stability of the knee joint. Such low level signals are described in Collins et al., U.S. Pat. No. 5,782,873.

Figure 7:
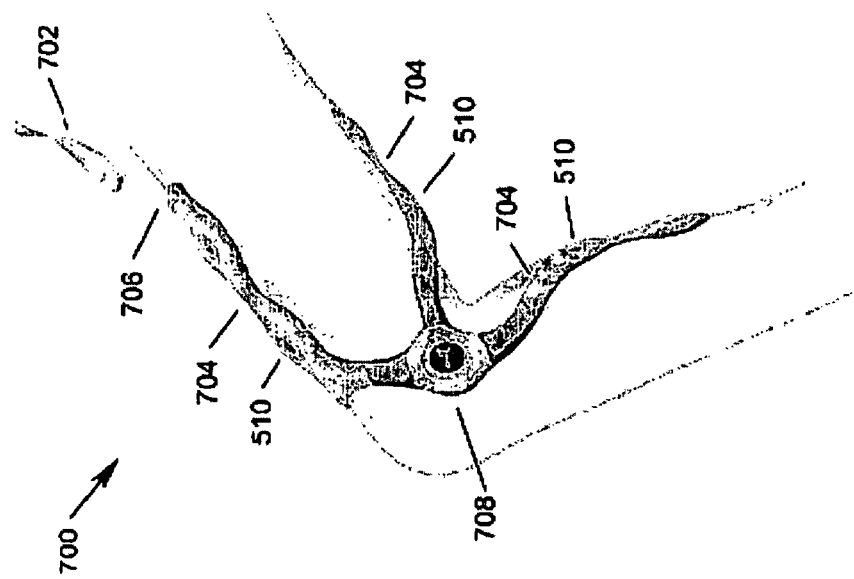
FIG. 7 illustrates wearable device, as one embodiment of the present invention.

In another preferred embodiment, provided is a structure 700 for placing signal input devices 510 in contact with the subject's skin, as shown in FIG. 7. A plurality of arms 704 extend from central hubs 708 which, when structure 700 is properly worn, are positioned on opposite sides of the joint of interest. The portion of arms 704 immediately adjacent to the central hubs 708 is composed of an expandable material, e.g. rubber. Arms 704 are preferably biased inwards inward to a degree, such as to securely engage the leg when structure 700 is positioned on the extremity. Arms 704 also include a plurality of input devices 510 positioned such that when structure 700 is properly positioned on the extremity, input devices 510 are positioned on those areas of the leg where the bias signal is to be applied in accordance with the method of the present invention.

At least one of the arms 704 includes a cable outlet 706 that is electrically wired to each of input devices 510. Outlet 706 accommodates electrical connector 702 of cable 512 such that when the other end of cable 512 is connected to signal generator 514, an electrical connection is established between signal generator 514 and input devices 510. Cable 512 is preferably composed of a stretchable and strain resistant material to reduce the likelihood of cable 512 becoming detached from outlet 706 or signal generator 514 during use.

Figure 8:
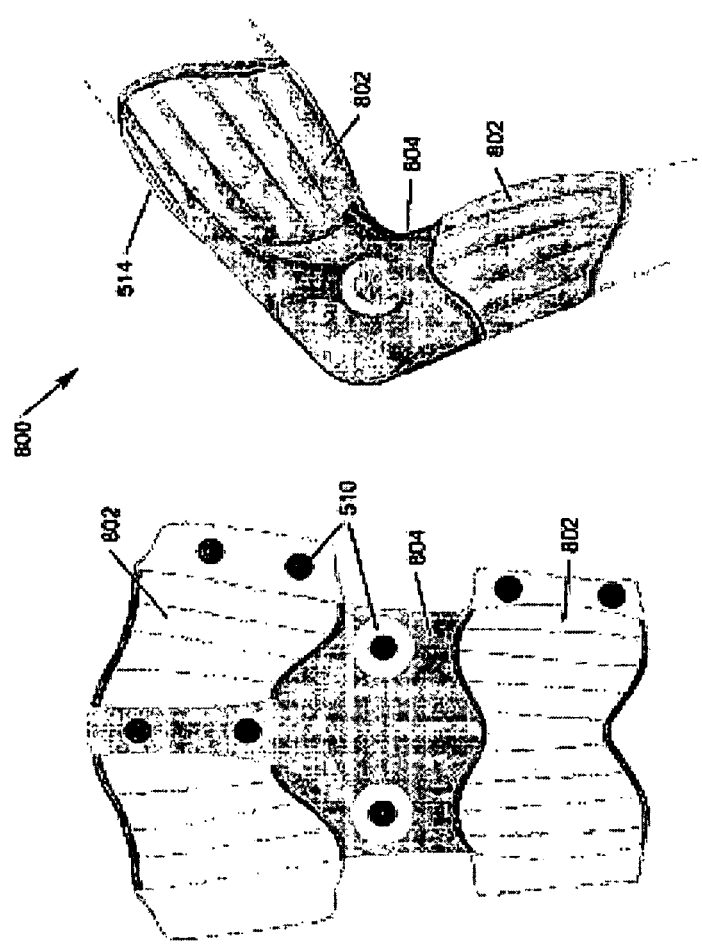
FIG. 8A-8B illustrate wearable device, as another embodiment of the present invention.

In another aspect of the invention, provided is a joint covering structure 800, as shown in FIGS. 8A-8B on a knee joint, having a plurality of input devices 510, and preferably a signal generator 514, incorporated into or positioned thereon. Input devices 510 are positioned so as to engage the appropriate combination of muscles and joints to which the bias signal is to be applied in accordance with the method of the present invention. Joint structure 800 is preferably designed to wrap around the joint and fasten upon itself by Velcro or other known fastening means. Alternatively, joint structure 800 can be configured to slide onto and off of the joint. Joint structure 800 is preferably made of fabric, but can also be made of plastic, rubber, or other material, as long as at least a portion of the structure is made of a flexible material which allows the input devices 510 to remain in place during the flexing and extending of the joint. As illustrated, the ridged portion 802 of structure 800 is comprised of thicker material capable of assistively bracing the joint. A thinner portion 804 of structure 800 is positioned over the joint so as to allow bending of the joint without displacing the input devices 510.

Figure 9:
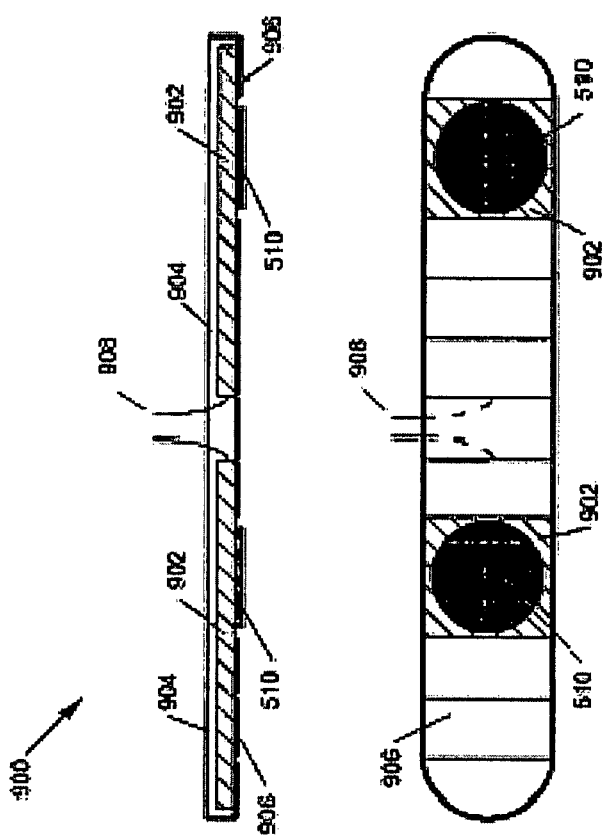
FIG. 9 illustrates a signal input device of the present invention.

In another aspect of the invention, provided is an electrode applicator 900, as shown in FIG. 9, which provides a means to customize the position of, or distance between, signal input devices 510 (e.g. skin surface electrodes) for a subject receiving treatment in accordance with the method of present invention. Areas of flexible, electrically conductive layer 902, such as conductive rubber, provide an electrically conductive means between wires 908 and signal input devices 510. Covering and surrounding the conductive layer 902 on the outer surface of the structure is a nonconductive material 904. These two layers of conductive 902 and non-conductive materials 904 are permanently affixed to one another. Also covering conductive layer 902 on its inner, or skin surface, side is a non-conductive film 906 which is removably affixed to the conductive layer 902. By removing non-conductive film 906, the inner surface of conductive layer 902 is exposed, allowing a signal input device 510 to be affixed to the conductive layer 902. Non-conductive film 906 is scored or otherwise segmented in a pattern which allows for portions of the non-conductive film 906, rather than the entire film, to be removed. In this way, the majority of the conductive layer 902 remains covered by the non-conductive film 906 during use. Signal input devices 510 are composed of a thin, electrically conductive material, such as hydrogel, that provides the electrical interface between the conductive layer 902 and the subject's skin.

The apparatus used for performing the method of the present invention is unique relative to known units used for improving sensorimotor performance (e.g. motor learning) or the treatment of injuries and rehabilitation from the effect of an injury. In such known units, electrodes are mounted on braces or wraps and include free, untethered electrical conductors, all of which will inhibit the motion required for the performance of an effective physical training regimen.

While the above illustrated embodiments are directed to pants, a joint stabilizer, and a brace, the term wearable device as used herein, refers to any structure capable of holding input devices 510 in place at a desired location.

The embodiments described herein have been shown as a lower body wearable device for illustrative purposes only. Similar embodiments capable of holding signal input devices in place that are designed to the upper body including the arms and torso of an individual, are within the spirit and scope of present invention. The upper body wearable device may be combined with the lower body wearable device to permit input devices to be positioned and operated simultaneously along both the upper and lower body in accordance with the method of the invention.

Figure 10A:
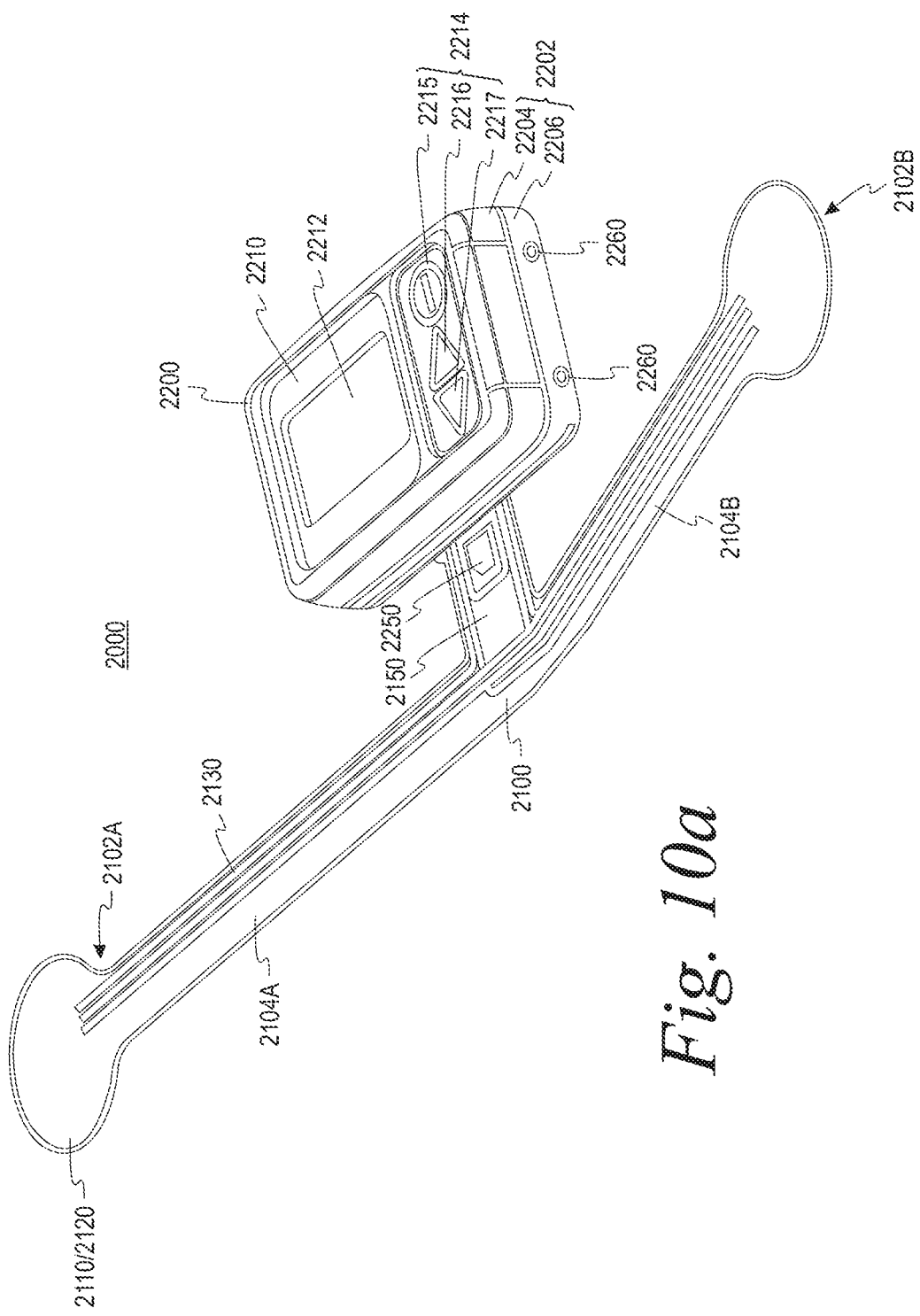
FIG. 10A illustrates an exemplary embodiment of a neuro-stimulation system, including a stimulator for delivering electrical and/or mechanical stimulation and a controller for driving the stimulator.
Figure 10B:
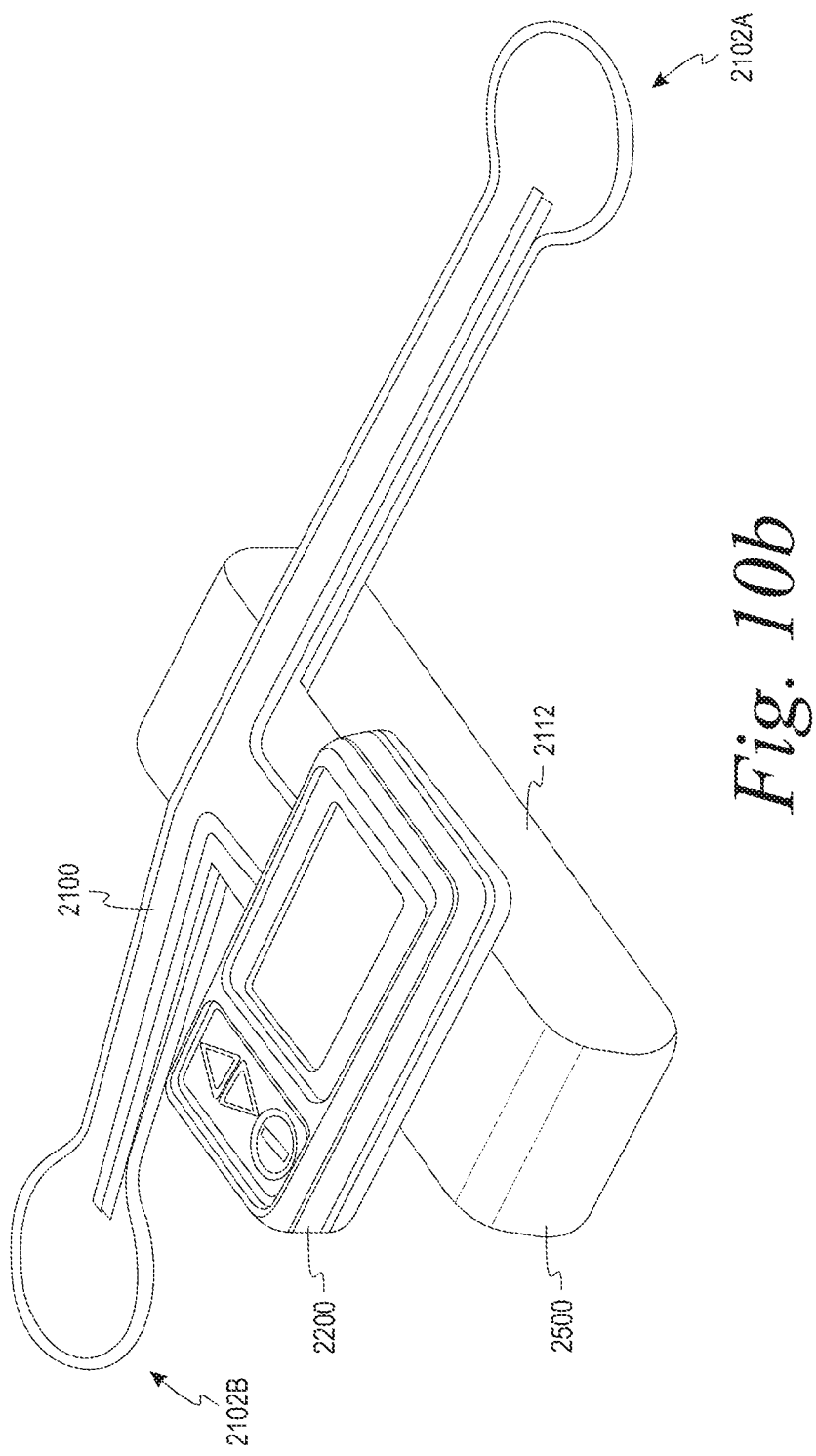
FIG. 10B illustrates the exemplary neuro-stimulation system of FIG. 10A coupled to an attachment element for securing the neuro-stimulation system to a body part.

Referring now to FIGS. 10A and 10B, a noninvasive, surface neuro-stimulation system 2000 is illustrated. The neuro-stimulation system 2000 may be applied to a patient non-sterilely and in an in-patient/out-patient setting. As shown, the neuro-stimulation system 2000 employs a stimulator 2100 and a controller 2200, which may be detachably coupled to each other. The stimulator 2100 is placed into contact with a body part of a subject, or patient, to deliver electrical current and/or mechanical vibration. The controller 2200 is operated to control the delivery of the electrical current and/or mechanical vibration through the stimulator 2100 according to the neuro-stimulation therapies described herein.

Advantageously, embodiments, such as the neuro-stimulation system 2000, enable the simultaneous use of electrical current and mechanical vibration to provide neuro-stimulation. In particular, the application of both electrical and mechanical stimulation provides broader targeting of mechanoreceptors. Electrical stimulation and mechanical stimulation reach different mechanoreceptors. For example, electrical stimulation may reach structures that lie deeper below a body part surface, while mechanical stimulation may reach structures that lie closer to the surface. A further unexpected benefit of applying both types of stimulation over the exclusive application of either electrical stimulation or mechanical stimulation is that all receptors are consistently activated during stimulation, and the body does not become confused by the activation of some receptors over other receptors in a particular sensory cell area.

Scientists and clinicians working in the field of stroke rehabilitation have established the critical link between mechanical sensory information (touch, pressure, and joint angle sense) produced during rehabilitation activities and the restoration of brain function. As such, in a preferred application, the neuro-stimulation system 2000 may be applied to rehabilitate stroke patients. Demonstrating the utility of such an application, a study in stroke rehabilitation was performed in an established animal model (developed by Dr. Jeffrey Kleim at the University of Florida).

The animal model used in the study reliably reproduces strokes in the motor cortex, so that post-stroke recovery of function may be quantified during a rehabilitation period. This model generally provides an excellent test-bed for comparing putative therapeutic interventions, which may include techniques, devices, or drugs. In this animal model, during a pre-stroke period which typically spans about 10 days, rats are trained to perform a task and they are graded according to their ability to perform the task. For example, the task may require the rats to reach around an obstacle to obtain food, and the rats are graded according to their proficiency, or accuracy, in reaching for food. At the end of the specified pre-stroke period, the rats are given a stroke in the motor cortex, and their task proficiency is measured over a period of several days after the stroke. According to clinicians, this animal model produces behaviors that are similar to those that the clinicians typically observe in stroke patients undergoing rehabilitation.

In this study, sensory enhancement stimulation was employed during rehabilitation to demonstrate that sensory enhancement stimulation improves neuroplasticity, or the formation of lasting functional changes in the brain. Using sixty animals in six treatment groups (including controls), the study tested whether sensory stimulation used in conjunction with physical rehabilitation would improve the reacquisition of skill versus rehabilitation without such stimulation. Stimulation below the sensory or motor threshold was delivered during rehabilitation sessions through implanted electrodes. Furthermore, three different stimulation amplitudes (RMS) were tested.

Figure 11:
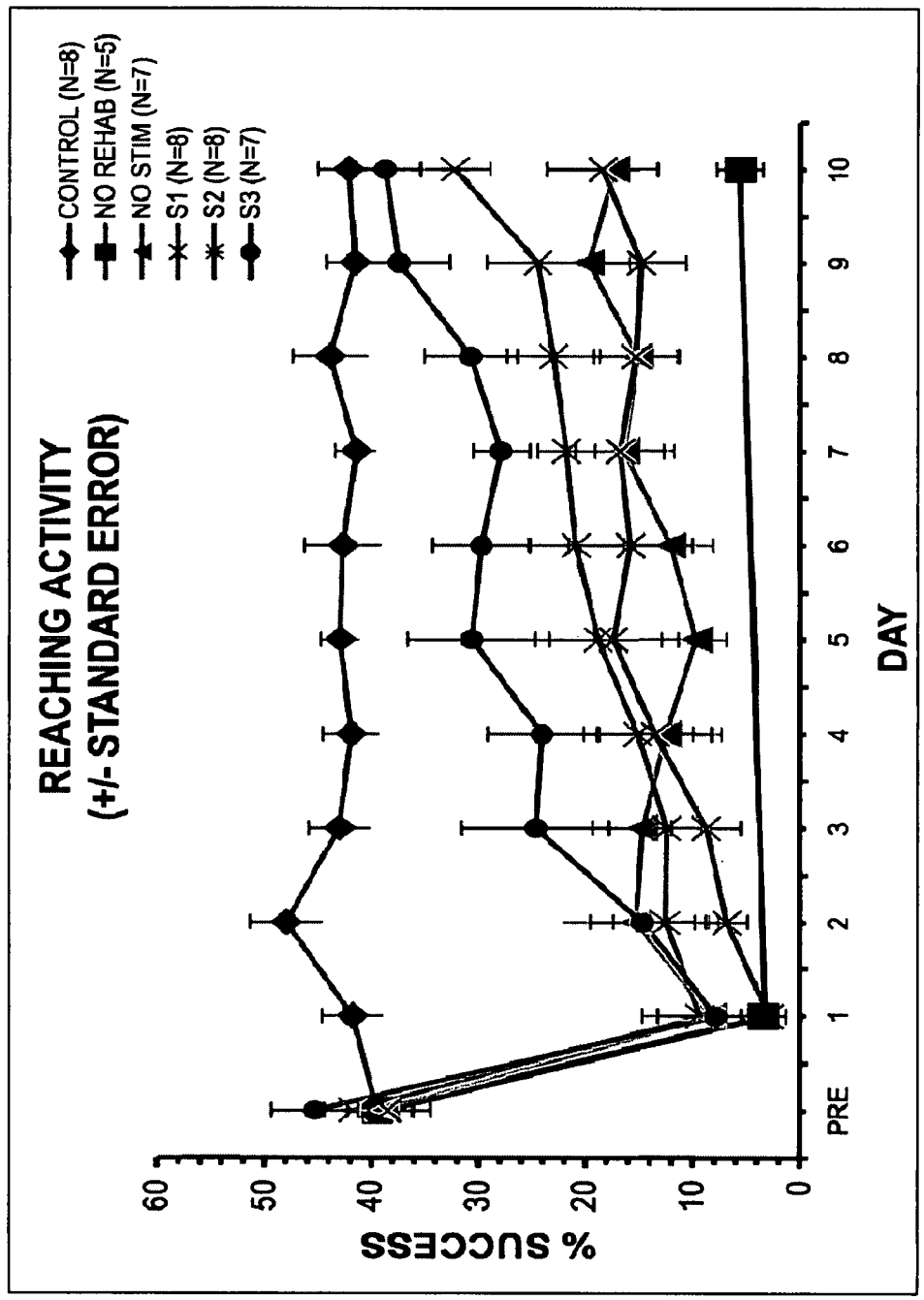
FIG. 11 illustrates a graph of success in executing a motor task versus time for six study groups in a stroke rehabilitation study examining the effects of sensory enhancement stimulation when applied during post-stroke rehabilitative therapy.
Figure 12:
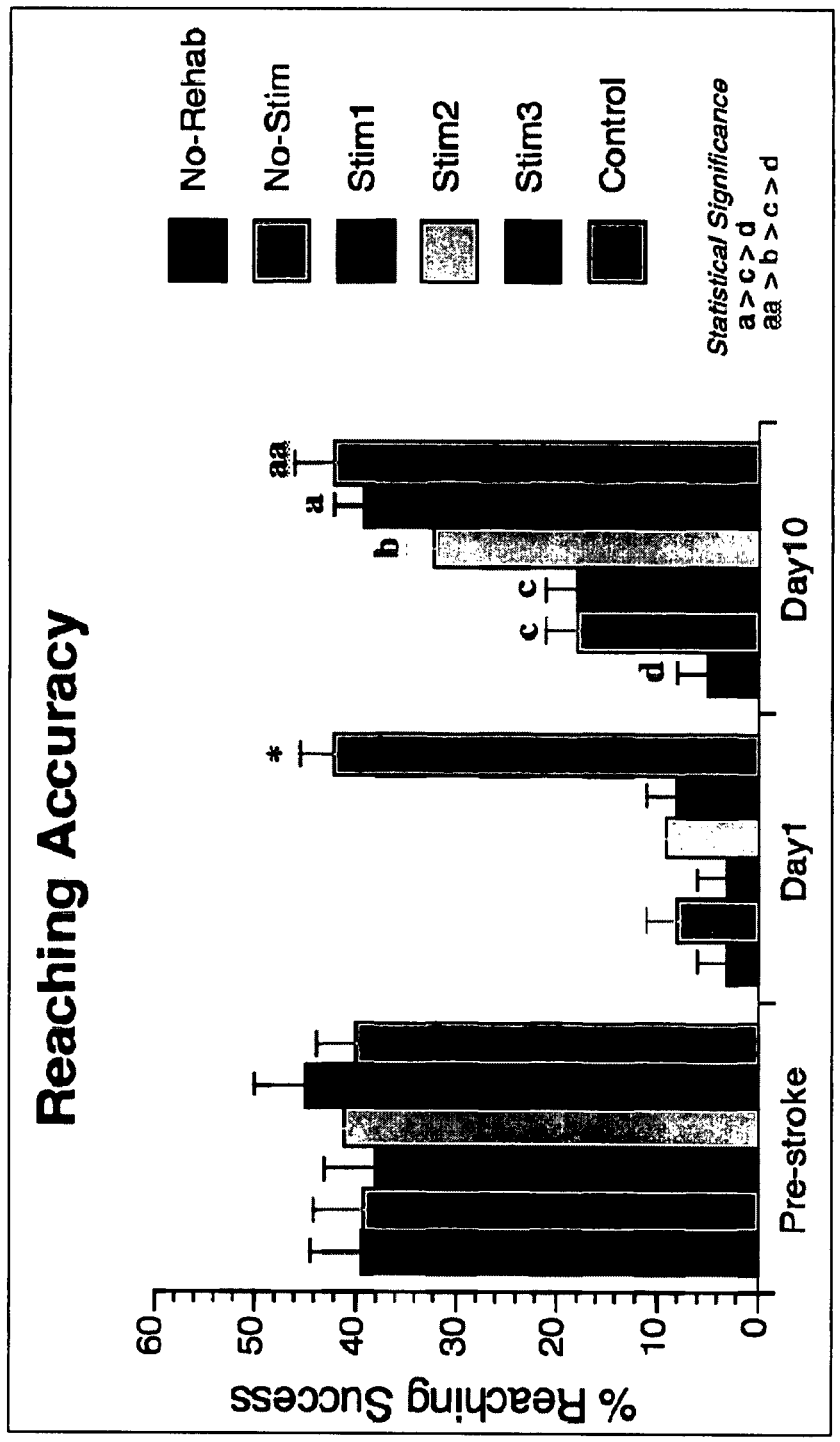
FIG. 12 illustrates yet another graph of success in executing a motor task versus time for the six study groups in the stroke rehabilitation study of FIG. 11.

The charts of FIGS. 11 and 12 present the resulting data for the six study groups in the study: a control group (no stroke), a group receiving no rehabilitation, a group receiving rehabilitation without stimulation, and three groups S1, S2, S3 receiving rehabilitation with three different amplitudes of stimulation, respectively. The charts indicate that the application of sensory enhancement stimulation in the study significantly accelerated and improved the endpoint in the reacquisition of skill when compared to rehabilitation without stimulation.

Accordingly, the neuro-stimulation system 2000 provides a tool for delivering sensory enhancement stimulation for improved stroke rehabilitation. For example, FIGS. 13A and 13B illustrate the application of the neuro-stimulation system 2000 to two respective location on a subject's arm for use during rehabilitative therapy. The neuro-stimulation system 2000 may be fitted with an attachment element 2500, such as the arm band also shown in FIG. 10B, that enables the neuro-stimulation system 2000 to be secured to the subject's arm as illustrated in FIG. 13. Of course, the neuro-stimulation system 2000 may employ other attachment elements and may be applied to other parts of the subject's body which may require rehabilitation.

Figure 14A:
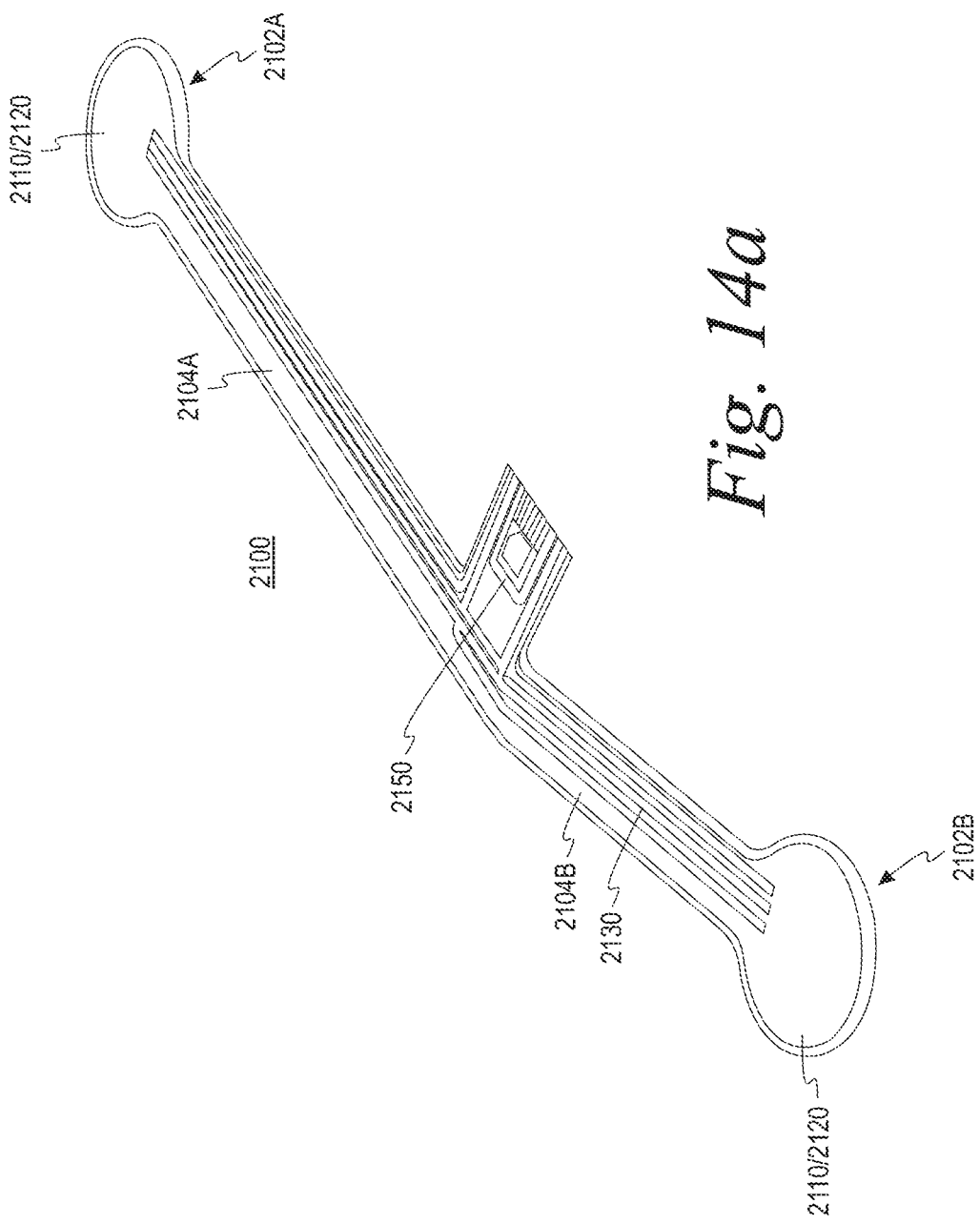
FIG. 14A illustrates the stimulator of the exemplary neuro-stimulation system of FIG. 10A.
Figure 14B:
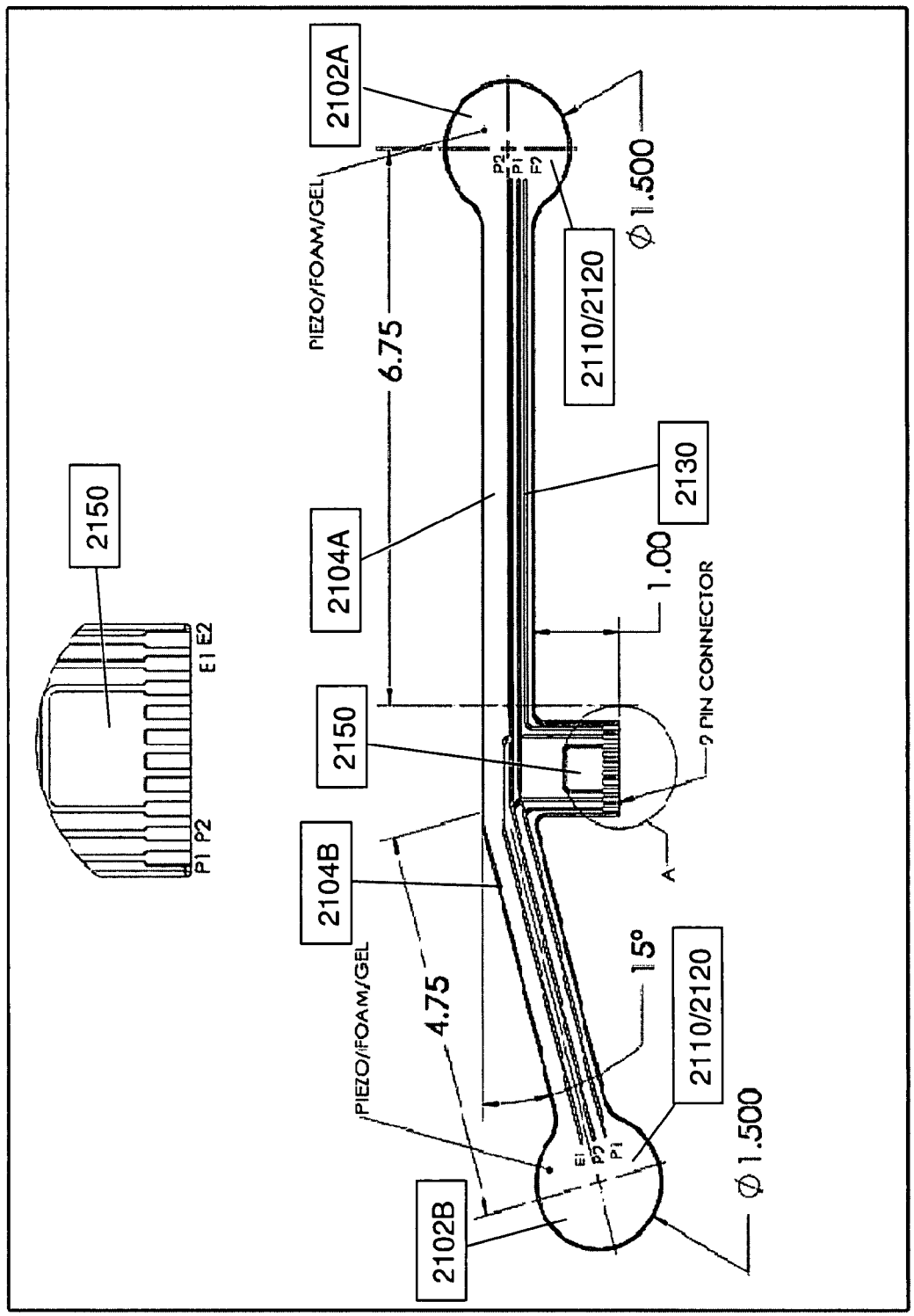
FIG. 14B further illustrates the stimulator of the exemplary neuro-stimulation system of FIG. 10A.

FIGS. 14A and 14B show an embodiment of a stimulator 2100. The stimulator 2100 has one or more contact areas 2102A and 2102B which are placed into contact with selected sites on the subject's body, and electrical and/or mechanical stimulation is delivered to the selected sites. As illustrated in FIG. 14A, the stimulator 2100 may be formed from laminated layers 2104, such as bonded layers of polycarbonate or the like, which can conform to a body part and enable sufficient contact with the selected stimulation sites.

In the particular embodiment shown in FIGS. 14A and 14B, the stimulator 2100 has a generally elongate shape with two contact areas 2102A and 2102B at opposing ends. As illustrated in detail in FIG. 14B, the contact area 2102A is positioned at the end of an arm 2104A that is approximately 7.5 inches long, while the contact area 2104B is positioned at the end of an arm 2104B that angles from the arm 2104A by approximately 15 degrees and is approximately 5.5 inches long. Moreover, the contact areas 2102A and 2102B are substantially circular with diameters of approximately 1.5 inches. As such, the shape shown in FIG. 14B accommodates application of the stimulator 2100 to a subject's arm as shown in FIG. 13. In general, however, a stimulator 2100 in other embodiments may have a shape that best accommodates its application to a particular body part, and thus the shape is not limited to the examples described herein.

Preferably, the stimulator 2100 employs at least one electrode device 2110 and at least one vibration element 2120 for delivering electrical and mechanical stimulation, respectively. As such, in the embodiment of FIGS. 14A and 14B, each of the contact areas 2102A and 2102B has electrode pair 2110 and a vibration element 2120. The electrode device 2110 refers to a source electrode and return electrode for electrical stimulation, although the source electrode and return electrode may be a part of an integral structure, or, alternatively, parts of separately applicable structures.

The electrodes 2110 may be screen-printed carbon and may be electrically connected to the stimulation site via a medical grade conductive hydrogel, such as a polyarylacetylene (PAA) hydrogel or similar material with biocompatibility data for skin contact. Preferably, electrical signals from the electrodes 2110 are only conducted through the contact areas 2102A and 2102B in contact with the stimulation areas. In the embodiment of FIGS. 14A and 14B, the electrodes at each contact area 2102A and 2102B may have a diameter of approximately 1.25 inches.

Additionally, adhesive may be employed on portions of the stimulator 2100 to secure the stimulator 2100 to the subject's body and position the contact areas 2102 at the selected stimulation sites. For example, a thin adhesive ring surrounding the gel at the contact areas 2102 may be employed to aid in securing the contact areas 2102 to the stimulation sites. A medical grade double sided adhesive with biocompatibility data for skin contact may be employed. In general, the adhesive properties of the stimulator 2100 as well as the supporting connection to the controller 2200 is adequate to support the stimulator 2100. Advantageously, the neuro-stimulation system 2000 also stays attached to the patient during therapy. In some cases, medical tape may be employed to aid in support. However, it is noted that the use of adhesive required to support the controller 2200 entirely may be too aggressive especially for the fragile skin of elderly patients. Thus, the use of an attachment element 2500, such as an arm band, may be preferred. A release liner (not shown) may be employed on the contact side of the stimulator 2100 to cover the hydrogel and adhesive and to ensure clean contact surfaces before application of the stimulator 2100 to the subject.

The vibration elements 2120 may be piezoelectric elements and may be mechanically coupled to the subject via the gel and surrounding adhesive. In the embodiment of FIGS. 14A and 14B, the vibration elements 2120 at each contact area 2102A and 2102B may have a diameter of approximately 1.25 inches and a maximum thickness of approximately 0.03 inches. The vibration elements 2120 may include two piezoelectric elements mounted side-by-side, and may be formed from lead zirconium titanate (PZT) mounted on a nickel plate.

Operation of the electrodes 2110 and the vibration elements 2120 is achieved through a circuit 2130. As shown in FIGS. 14A and 14B, a flex circuit 2130 is routed throughout the stimulator 2100 to connect the electrodes 2110 and the vibration elements 2120 to the controller 2200. For example, the flex circuit 2130 may employ low resistance silver (Ag) or silver/silver chloride (Ag/AgCl).

Additionally, the stimulator 2100 may employ an internal electrically-erasable read-write memory device 2140, such as an EEPROM, which is connected to the flex circuit 2130. The flex circuit 2130 provides power, ground, and signals to the memory device 2140. The memory device 2140 records and stores data on the operation of the stimulator 2100. As described further below, the controller 2200 may write data to the memory device 2140 when the stimulator 2100 is coupled to the controller 2200.

In some cases, to ensure the proper functioning of each stimulator 2100, the stimulator 2100 may have a specified shelf life, e.g. one year. In addition, the stimulator 2100 may be limited to a single use, after which it must be discarded. Furthermore, to prevent overuse during a single application, each stimulator 2100 may have a specified stimulator life, e.g. three hours, which sets the maximum amount of time the stimulator 2100 may be used during the single use. In one embodiment, the controller 2200 may be employed to prevent repeated use of the stimulator 2100 and to track the stimulator's total amount of use against the specified stimulator life. In particular, as described further below, the controller 2200 may store usage data regarding the use of a stimulator in the memory device 2140.

While the stimulator 2100 may be limited to a single use and a maximum usage time on the order of a few hours, the controller 2200 may have a significantly longer life. For example, the design life for the controller 2200 may be approximately four years, with annual battery replacement. As such, the controller 2200 is generally reusable. On the other hand, due to the limits on its use, a single stimulator 2100 is disposable and not reusable. Therefore, a single controller 2200 is typically used with a plurality of stimulators 2100.

The stimulator 2100 has a connector 2150 that enables the stimulator 2100 to be detachably coupled to the controller 2200. Electrical signals may be sent and/or received via the connector 2150. As such, the connector 2150 connects the flex circuit 2130 to the controller 2200. In the embodiment of FIGS. 14A and 14B, the connector 2150 may be an n-pin connector, e.g. 9-pin connector, approximately 1 inch long.

As shown in FIG. 15B, the controller 2200 has a connection port 2250 which correspondingly receives, or engages, the connector 2150 of the stimulator 2100. For example, the connection port 22 may receive the nine pins for the connector 2150 shown in FIG. 15B. Through this connection with the stimulator 2100, the controller 2200 may control the delivery of electrical and/or mechanical stimulation by the stimulator 2100.

FIGS. 15A and 15B show that the controller 2200 has a housing 2202 which is defined by the assembly of a front housing section 2204 and a back housing section 2206. The housing sections 2204 and 2206 may be molded from a material such as acrylonitrile butadiene styrene (ABS) or the like. In the embodiment of FIGS. 15A and 15B, the controller 2200 may have overall dimensions of approximately 3.5"×2.5"×1.25" and may have an overall weight of approximately 100 g. As such, the controller 2200 is sufficiently lightweight and compact for easy application, as particularly shown in FIG. 13.

FIG. 15A illustrates a user interface 2210 positioned on a side of the front housing section 2204. The user interface 2210 may include a graphic display 2212 for presenting operational information to a user and input controls, such as a light-touch membrane keypad 2214, for receiving operational instructions from a user.

In particular, the graphic display 2212 may provide the user with information regarding the status of the stimulator life, battery life, stimulation time, and the electrical and stimulation output levels. For example, in the embodiment of FIGS. 15A and 15B, the graphic display 2212 may be a monochrome graphic display with 128 (W)×64 (H) pixels, which provide yellow, blue, green, or similarly colored graphic elements on a black background. As such, the graphic display 2212 may employ an organic light emitting diode (OLED). The overall dimensions of the graphic display may be approximately 1.9"×1.3".

Meanwhile, as shown in FIG. 15A, the keypad 2214 may have a power key 2215 to allow the user to turn the controller on and off. In addition, the keypad 2214 may have adjustment keys 2216 and 2217 to adjust the stimulation levels up and down, respectively. As discussed further below, the keys 2215, 2216, and 2217 may be employed in a variety of sequences or combinations to provide input for the operation of the controller 2100. The keypad 2214 may be a membrane keypad formed, for example, from polycarbonate or the like. In the embodiment of FIGS. 15A and 15B, the overall dimensions of the keypad may be approximately 1.5"×0.75".

FIG. 15B also shows that a clip 2208, or other similar structure, may be positioned on a side of the back housing section 2206 to work with an attachment element 2500 for securing the controller 2200 to the subject. For example, the clip 2208 may be employed to attach the controller 2200 to the arm band 2500 described previously with reference to FIG. 10B.

Figure 16:
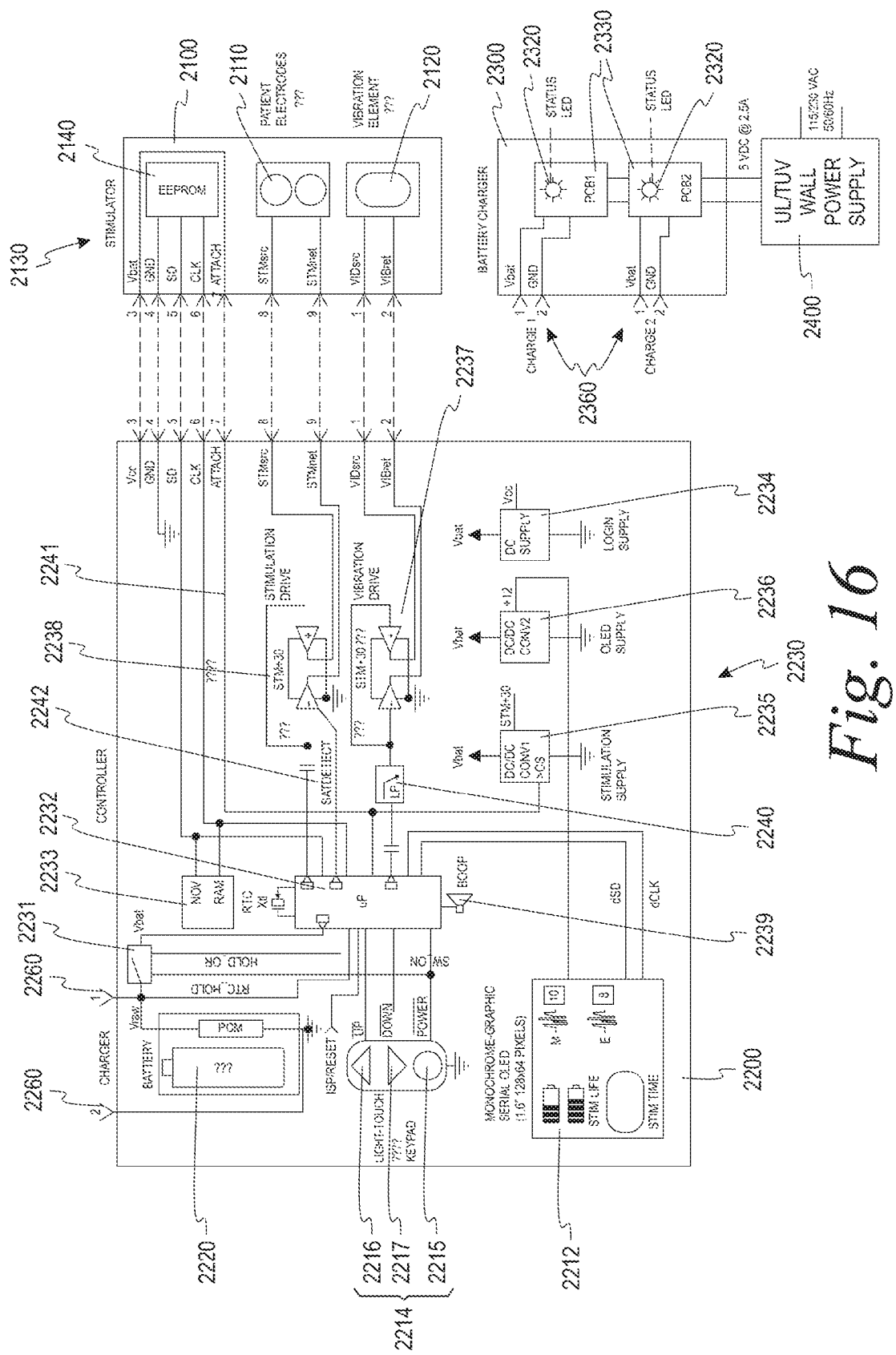
FIG. 16 illustrates the circuit of the exemplary neuro-stimulation system of FIG. 10A.

The diagram of FIG. 16 illustrates electrical components and connections that may be employed for the neuro-stimulation system 2000. It is understood, however, that FIG. 16 merely presents an example embodiment, and in no way limits the electrical components and connections that may be employed in other embodiments.

As shown in FIG. 16, the controller 2200 houses a power supply 2220 and an embedded processor 2230, which are connected to each other. The processor 2230 is also connected to the graphic display 2212 and the keypad 2214. In the embodiment of FIG. 16, the flying leads of power supply 2220 may be directly soldered for connection to the processor 2230. The graphic display may be connected via 0.5 mm SMT ZIF (18 conductor), and the keypad 2214 may be connected via 1 mm SMT ZIF (4 conductor).

The power supply 2220 generates the required voltage and current for operating the processor 2230 as well as the electrodes 2110, the vibration elements 2120, and the graphic display 2212. For example, the power supply may be a lightweight rechargeable lithium ion battery pack. However, in other embodiments, the neuro-stimulation system 2000 may employ disposable non-rechargeable batteries or other types of power sources. Generally, a lightweight portable power supply 2220 is preferred over sources such as an electrical outlet to make the controller 2200 also lightweight and portable. In the embodiment of FIG. 16, battery 2220 may have a nominal voltage of 3.6 VDC. With a minimum capacity of approximately 1,600 mAh, the battery 2220 may provide approximately 3 hours of run time between charges. With a charge voltage of 4.2 VDC, the charge time for the rechargeable battery 2220 may be approximately 4 hours. As known, the battery 2220 may include an internal power control module to minimize over charge/discharge. For repeated use of the rechargeable battery 2220, the battery 2220 is chargeable to preferably at least 75% of original capacity after 500 cycles.

The display, keypad, mechanical stimulation, and electrical stimulation are controlled by the processor 2230. The processor 2230 may, for example, be a central printed circuit board (PCB) formed from G-10 which serves as the central point of connectivity and contains all the hardware and software required to generate and control the stimulation applied through the stimulator 2100. In the embodiment of FIG. 16, the processor 2230 includes: a field-effect transistor switch (FET SW) 2231; a microcontroller (μC) 2232 with non-volatile random access memory (nov-RAM) 2233; a DC supply 2234; DC-to-DC converters 2235 and 2236; a mechanical stimulation drive 2237; an electrical stimulation drive 2238; and a sound device 2239.

In the embodiment of FIG. 16, the keypad 2214 may employ four circuits corresponding with the power key 2215, up and down adjustment keys 2216 and 2217, as well as ground. The keypad 2214 may employ TTL level signals, as well as single pole single throw (SPST) switches which are normally open.

When the power key 2215 on the keypad 2214 is pressed, the FET switch 2231 is correspondingly turned on and power from the power supply 2220 is provided via the FET switch 2231 to the rest of the controller 2200. Once the microcontroller 2232 receives power and is activated, it holds the FET switch 2231 on. When the microcontroller 2232 determines a shut down, it turns the FET switch 2231 off. In the embodiment of FIG. 16, the FET switch 2231 may employ signal level controls and may have a rating of 4.2 V at 500 mA (min).

The microcontroller 2232 with the non-volatile memory 2233 hosts the firmware and provides overall control for the neuro-stimulation system 2000. The microcontroller 2232 may be a single chip microcontroller, which has a speed that is sufficient to support the input/output and the random signal generation described herein. The features of the microcontroller 2232 may include: integrated power on reset circuitry, integrated clock oscillator, integrated RAM and program memory, internal RTC with external xtl, integrated 12-bit analog-to-digital converter, two integrated 12-bit digital-to-analog converters, integrated voltage reference, and sufficient digital signal processing (DSP) capability to support white noise generation and filtering (10 Hz-100 Hz).

In addition, the microcontroller 2132 has sufficient input/output (I/O) capacity to support: input from a battery voltage monitor, input from power key 2115, input from up and down adjustment keys 2116 and 2117, input from the stimulator 2100 for StimEnable and SatDetect signals described herein, input and output from the non-volatile RAM 2233, input and output from the EEPROM 2140 of the stimulator 2100, input and output from the graphic display 2112, ISP input, output for the sound device 2239, output for the mechanical stimulation drive 2237, and output for the electrical stimulation drive 2238.

In the embodiment of FIG. 16, the microcontroller 2232 may have an output current of approximately 100 mA (min) and may have a regulation of +/−1% ripple. Moreover, the programming of the microprocessor 2232 may employ ISP. Meanwhile, non-volatile RAM 2233 provides a minimum of four kilobytes with a memory address of 0xA0 and a serial memory interface.

The processor 2230 includes the DC supply 2234, which receives input voltage ($V_{bat}$) from the power supply 2220 and produces regulated and filtered voltage for the control circuitry. In the embodiment of FIG. 16, the DC supply 2234 receives a nominal input battery voltage from the power supply 2220 of approximately 3.6 VDC, and may produce an output voltage of approximately 3.0 VDC and output current of 100 mA (min). Furthermore, the DC supply 2234 may have a regulation of +/−1% ripple.

The processor 2230 may also employ a sound device 2139, such as a signal level audio transducer, that sounds or beeps when the keypad is pressed or during an alert or alarm condition. In the embodiment of FIG. 16, the sound device 2135 may have an audio output level of at least 60 dB at 30 cm.

In addition, the processor 2230 also includes the DC-to-DC converter 2235, which receives input voltage from the power supply 2220 and generates the higher voltage rails required to drive the electrical and mechanical stimulation circuitry, described further below. In the embodiment of FIG. 16, the DC-to-DC converter 2235 may receive an input voltage ($V_{bat}$) of approximately 3 VDC and produce an output voltage of approximately 30 VDC and an output current of approximately 30 mA (typ) for the delivery of electrical and mechanical stimulation.

Furthermore, the processor 2230 also includes the DC-to-DC converter 2236, which receives input voltage from the power supply 2220 and generates the voltage for operation of the graphic display 2112. In the embodiment of FIG. 16, the DC-to-DC converter 2236 may receive an input voltage ($V_{bat}$) of approximately 3 VDC and produce an output voltage of approximately 12 VDC and an output current of approximately of +/−500 mA (typ) for the graphic display 2112. The data transfer to the graphic display 2112 may be serial. The logic voltage may be approximately 2.4 VDC to 3.5 VDC and the supply voltage may be approximately 12 VDC (typ).

Receiving the voltage from the DC-to-DC converter 2235, the mechanical stimulation drive 2237 and the electrical stimulation drive 2238 provide the output to drive the vibration elements 2120 and the electrodes 2110 of the stimulator 2100. In particular, the microcontroller 2232 generates, sets amplitude, filters, and delivers the aperiodic signal that drives the vibration elements 2120 and the electrodes 2110.

In the embodiment of FIG. 16, an H-Bridge amplifier configuration is used to push and pull the outputs. The mechanical stimulation drive 2237 may employ voltage control. The digital-to-analog conversion may be 10 bit (min), or equivalent resolution. The voltage-to-voltage conversion may be: 1.3 V in=+30 V out; 650 mV in=0 V out; 0 V in=−30 V out; 0 to 1.3 V. With an input voltage of 0 to 1.3 V, the output voltage may be: −30 V to +30 V (max, +/−3 sigma); −20 V to +20 V (+/−2 sigma); −10V to +10V (typ, +/−1 sigma). The output current may be −30 mA to +30 mA (max). The waveform produced by the mechanical stimulation drive 2237 is aperiodic with a Gaussian distribution and the frequency spectrum may be 10 Hz (or lower) to 100 Hz. Filtering may have a pass band ripple of less than 0.5 dB and equivalent roll off above 100 Hz to a 6-pole Butterworth. Output may also need additional low pass filtering due to a 1 ms pulse width. Thus, a low pass (LP) filter 2240 provides additional filtering to "smooth out" the 1 ms pulse width transitions in the vibration drive. The LP filter 2240 may employ a 3 Pole Chebychev, with a pass band of 10 Hz to 125 Hz.

In the embodiment of FIG. 16, the electrical stimulation drive 2238 may employ current control. The digital-to-analog conversion may be 10 bit (min), or equivalent resolution. The voltage-to-current conversion may be: 1.3 V in=+150 µA out; 650 mV in=0 µA out; 0 V in=−150 µA out. With an input voltage of 0 to 1.3 V, the output current may be: −150 µA to +150 µA (max, +/−3 sigma); −100 µA to +100 µA (+/−2 sigma); −50 µA to +50 µA (typ, +/−1 sigma). The output voltage may be −30 V to +30 V (max). The waveform produced by the electrical stimulation drive 2238 is aperiodic having a Gaussian distribution with a hold output of 1 ms/level, while the spectrum is defined by the 1 ms hold time (no additional filtering is required). The hardware current limit is +/−150 µA. A SatDetect signal 2242 is issued if the target current cannot be achieved (skin Z is too high) or if the electrodes are not connected.

Figure 20A:
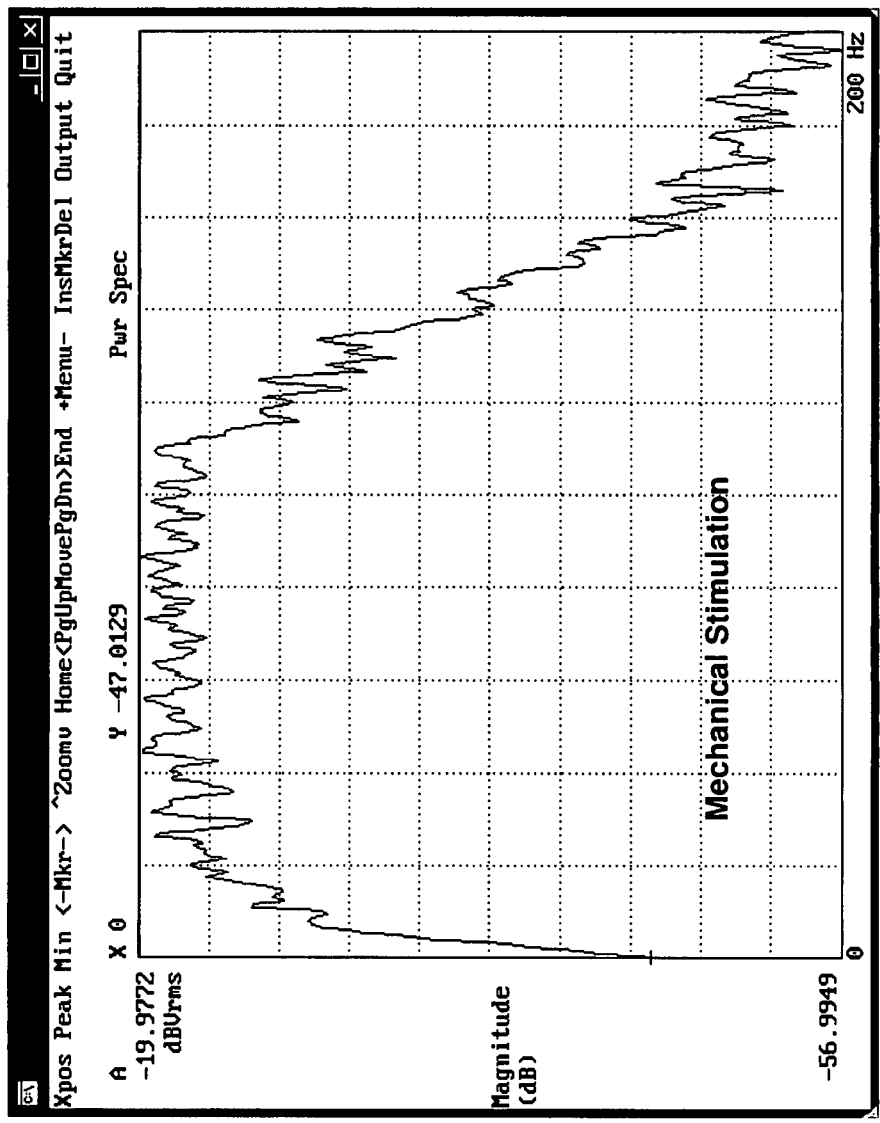
FIG. 20A illustrates a chart of the spectral content of exemplary mechanical stimulation for an exemplary embodiment of a neuro-stimulation system.
Figure 20B:
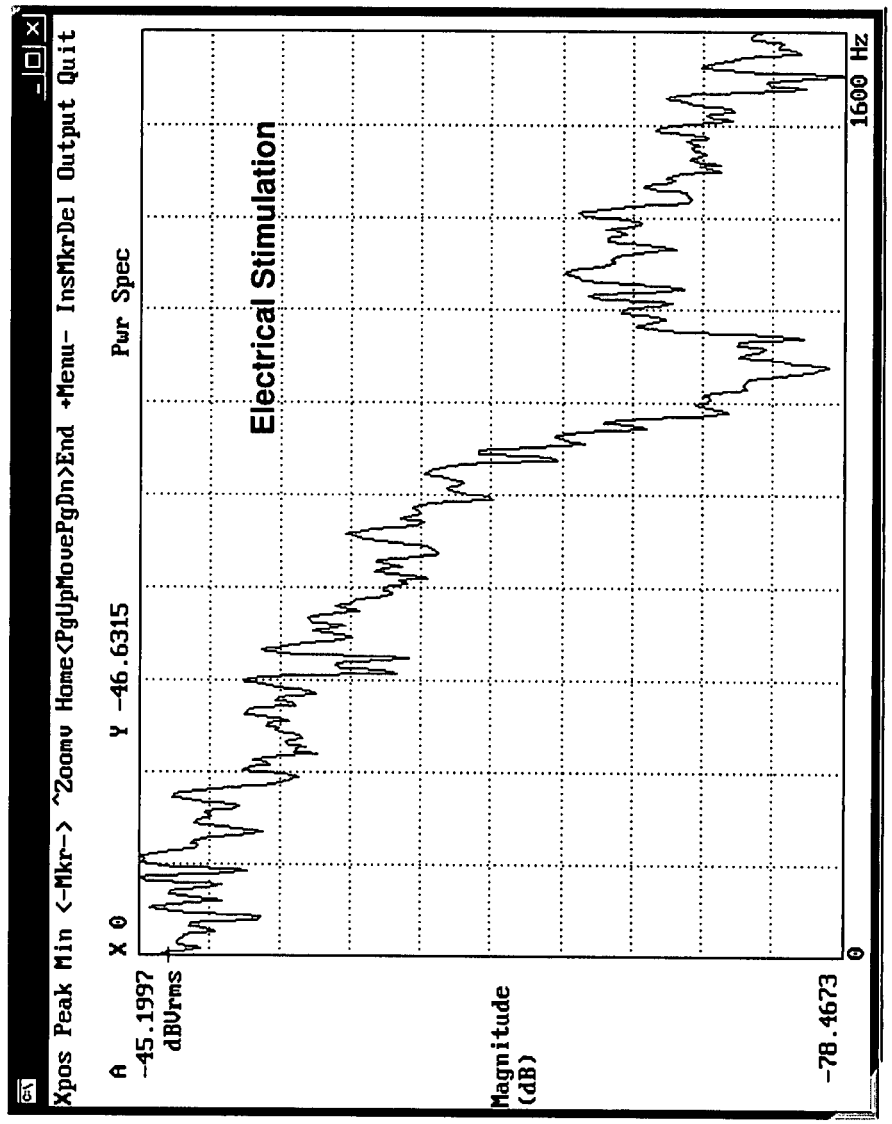
FIG. 20B illustrates a chart of the spectral content of exemplary electrical stimulation for an exemplary embodiment of a neuro-stimulation system.
Figure 20C:
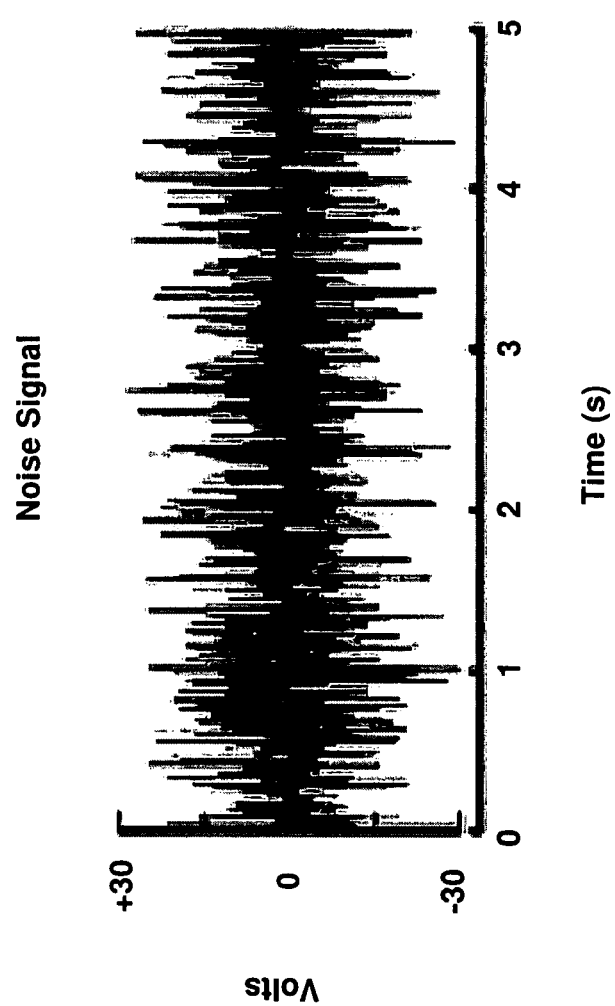
FIG. 20C illustrates a chart of exemplary random noise signal corresponding to stimulation by an exemplary embodiment of a neuro-stimulation system.

The graphs in FIGS. 20A-C represent aperiodic outputs which may be produced by the mechanical stimulation drive 2237 and the electrical stimulation drive 2238. FIGS. 20A and 20B demonstrate that the spectral content of the mechanical stimulation and the electrical stimulation, respectively, is within a defined narrow band, while FIG. 20C shows that output is random over time. Advantageously, both the randomness and the frequency content enable targeting of the appropriate receptors. In other words, different receptors may respond to different stimulation frequencies, so the aperiodic stimulation helps to promote a response from receptors which may have such varying response characteristics. As a further advantage, by randomly and unpredictably applying a range of frequencies, aperiodic stimulation avoids the effect of adaptation where the response to specific frequencies diminishes, or is wiped out, with repeated and predictable exposure to the same specific frequencies. As shown in FIG. 20C, the noise is normally distributed about a mean, so the signal may be electrically expressed as a Gaussian distribution. The aperiodic sequence preferably does not repeat itself within 20 seconds.

In the embodiment of FIG. 16, the stimulation output from the microcontroller 2231 is a current, with maximum value of 0.5 mA. When converted to a voltage signal across a 2.61 kΩ sense resistor the input to both the mechanical stimulation drive 2237 and the electrical stimulation drive 2238 is biased to 0.65 VDC. Therefore, a setting of 100% represents waveforms that span the entire range, i.e. 0 VDC to 1.3 VDC. A 50% setting in either electrical or mechanical stimulation spans an output range of 0.325 VDC to 0.975 VDC.

The output from the mechanical stimulation drive 2237 and/or the electrical stimulation drive 2238 of the processor 2230 is transmitted to the stimulator 2100 via the detachable coupling of the connection port 2250 and the connector 2150. As described previously, this coupling may employ a 9-pin connection. The mechanical stimulation drive 2237 drives the vibration elements 2120 of the stimulator 2100, while the electrical stimulation drive 2238 drives the electrodes 2110 of the stimulator 2100.

With further reference to the embodiment of FIG. 16, the electrodes 2110 may employ dual carbon electrodes with a resistance of 500 ohms (max) (measured from each electrode surface to contact with the flex circuit). The vibration elements 2120 may employ two parallel piezo elements, with piezoelectric bimorph technology. The input power to the vibration elements 2120 may be approximately 150 mW (max), and the oscillating range of the vibration elements 2120 may be approximately DC to 20 kHz.

In the embodiment of FIG. 16, the stimulator 2100 employs an EEPROM 2140. The EEPROM 2140 may have a size of 1 K (128×8) (min) with a memory address of 0xA1. The power supply to the EEPROM 2140 may be approximately 1.8 to 5.5 VDC. The package for the EEPROM 2140 may be 8 pin, SOIC SMT. For chip select, the A0 address bit must be decoded.

When the stimulator 2100 is connected to the controller 2200, the EEPROM 2140 may be serially connected to the processor 2130, so that the processor 2230 may read and write to the EEPROM 2140. In particular, as described previously, the controller 2200 may employ the EEPROM 2140 to track usage data, such as the total amount of use against a specified stimulator life for the stimulator 2100.

Additionally, as further illustrated by FIG. 16, the flex circuit 2130 provides a way for the controller 2200 to detect the presence of the stimulator 2100 by shorting pin 3 ($V_{bat}$) to pin 7. As such, when the stimulator 2100 is attached to the controller 2200, the StimEnable line 2241 goes high, informing the microcontroller 2232 to switch on the DC-to-DC converter 2235 (30 V step up) to power the mechanical stimulation drive 2237 and electrical stimulation drive 2238.

Figure 17:
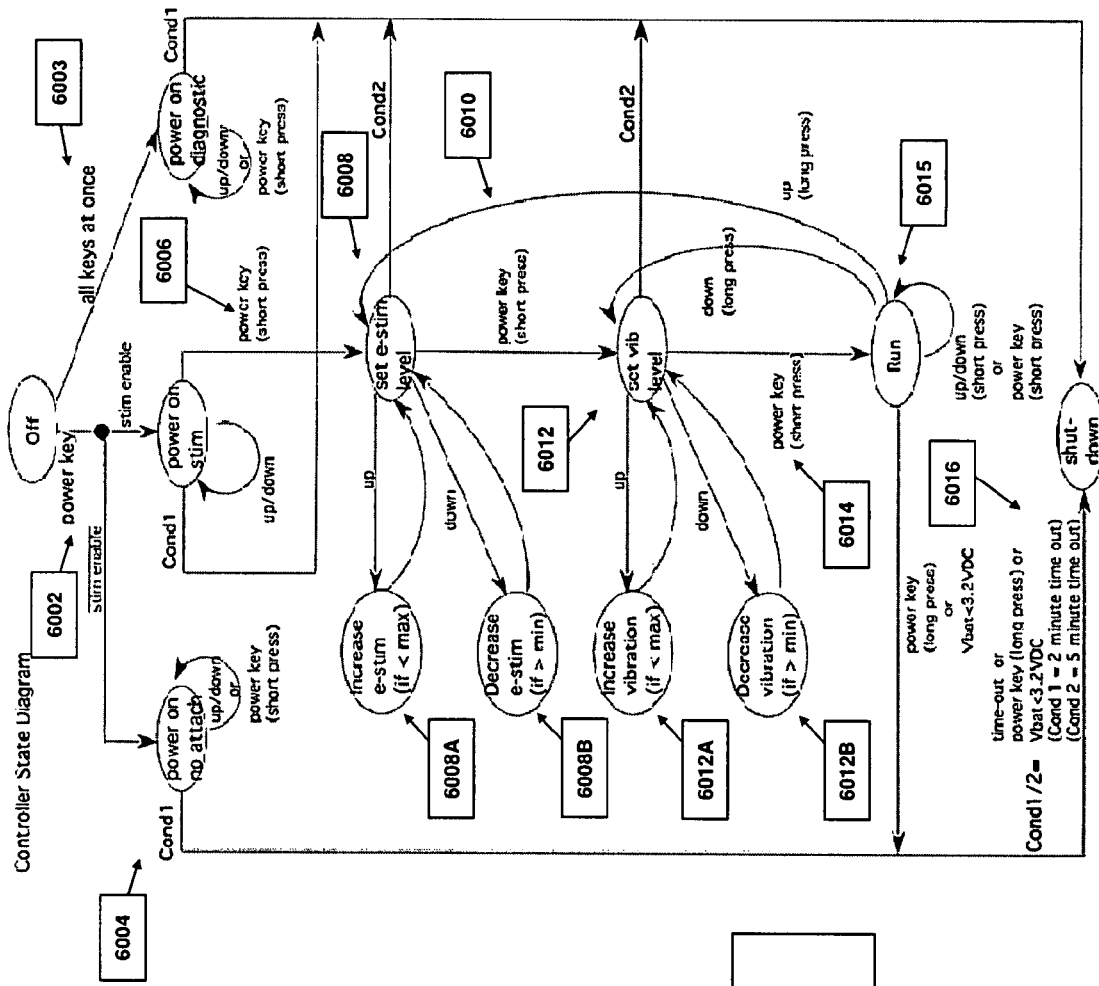
FIG. 17 illustrates an exemplary method for operating the exemplary neuro-stimulation system of FIG. 10A.

FIG. 17 illustrates a controller state diagram and operation of the example embodiment shown in FIG. 16. As such, the state diagram of FIG. 17 merely presents a non-limiting example of operation of the neuro-stimulator 2000.

Operation of the controller 2200 is governed by the embedded software of processor 2230. In step 6002, the power key 2215 is operated, or pressed, to power up the controller 2200. As described previously, the processor 2230 is able to detect whether a stimulator 2100 is coupled to the controller 2200. If the controller 2200 is not connected to a stimulator 2100, the graphic display 2112 displays the life of battery 2220 in step 6004 and the controller 2200 shuts down automatically after 2 minutes, as described further below. Otherwise, when the controller 2200 powers up, the graphic display (OLED) 2112 displays the life of battery 2220 and life of the stimulator 2100.

In step 6006, the power key 2115 is pressed again to allow the electrical stimulation with the stimulator 2100 to be set, in step 6008. In step 6008A, the up adjustment key 2116 may be pressed to increase the electrical stimulation up to any value below a predetermined maximum, e.g. 100%. For example, pressing the up adjustment key 2116 once increases the electrical stimulation by 5% of its entire range. On the other hand, in step 6008B, the down adjustment key 2117 may be pressed to decrease the electrical stimulation down to any value above a predetermined minimum, e.g 0%. For example, pressing the down adjustment key 2117 once decreases the electrical stimulation by 5% of its entire range. In response to step 6008, the processor 2230, with the electrical stimulation drive 2238, drives the electrodes 2110 of the stimulator 2100 with a current that corresponds with the given setting. When the electrical stimulation level is changed, with the up and down adjustment keys 2116 and 2117 and even shutdown with the power key 2115, the change is preferably executed in a ramped manner. A sudden change may be perceived as uncomfortable to the patient. As such, a slew rate of approximately 0.2 μA/ms (or 1 μA every 5 ms) may be employed.

In step 6010, the power key 2115 is pressed again to allow the mechanical stimulation with the stimulator 2100 to be set, in step 6012. In step 6012A, the up adjustment key 2116 may be pressed to increase the mechanical stimulation up to any value below a predetermined maximum, e.g. 100%. For example, pressing the adjustment key 2116 once increases the mechanical stimulation by 5% of its entire range. In step 6012B, the down adjustment key 2117 may be pressed to decrease the mechanical stimulation down to any value above a predetermined minimum, e.g. 0%. For example, pressing the adjustment key 2117 once decreases the mechanical stimulation by 5% of its entire range. In response to step 6012, the processor 2230, with the mechanical stimulation drive 2237, drives the vibration elements 2120 of the stimulator 2100 with a voltage that corresponds with the given setting.

In step 6014, the power key 2115 is pressed again to lock the stimulation levels set in steps 6008 and 6012. Electrical and/or mechanical stimulation continues in run mode 6015 with the set values.

Step 6016 evaluates conditions for shut down and causes automatic shut down of the controller 2200 when the conditions are met. These conditions are indicated by "Cond 1" and "Cond 2" in FIG. 17.

Thus, during the run mode 6015, the power key 2115 may be pressed and held for a specified duration, e.g. two seconds, to cause the controller to be turned off in step 6016. The controller 2200 does not exit run mode 6015 until the power key 2115 is pressed for the specified duration.

In addition, the voltage of the battery 2220 is also measured during operation. If the remaining charge in battery 2220 falls below 3.2 V, for example, the controller 2200 automatically shuts down in step 6016.

As described previously, the processor 2230 holds the FET switch 2231 on. However, in step 6016, the FET switch 2231, and thus the controller 2200, may be turned off automatically in the following time-out situations:

the power key 2115 has not been pressed for a period of time, e.g. 2 minutes, to advance to step 6008 after the controller 2200 has been powered up in step 6002.

the power key 2115 has not been pressed for a period of time, e.g. 5, minutes, to advance to step 6012 after the level of electrical stimulation has been set in step 6008.

the power key 2115 has not been pressed for a period of time, e.g. 5 minutes, to advance to run mode 6015 after the level of mechanical stimulation has been set in step 6012.

no keys are pressed for a period time, e.g. 2 minutes, after the controller 2200 has been powered up in step 6002 and no stimulator 2100 is coupled to the controller 2200.

no keys are pressed for a period of time, e.g. 2 minutes, after the diagnostic mode has been executed in step 6003.

Figure 18:
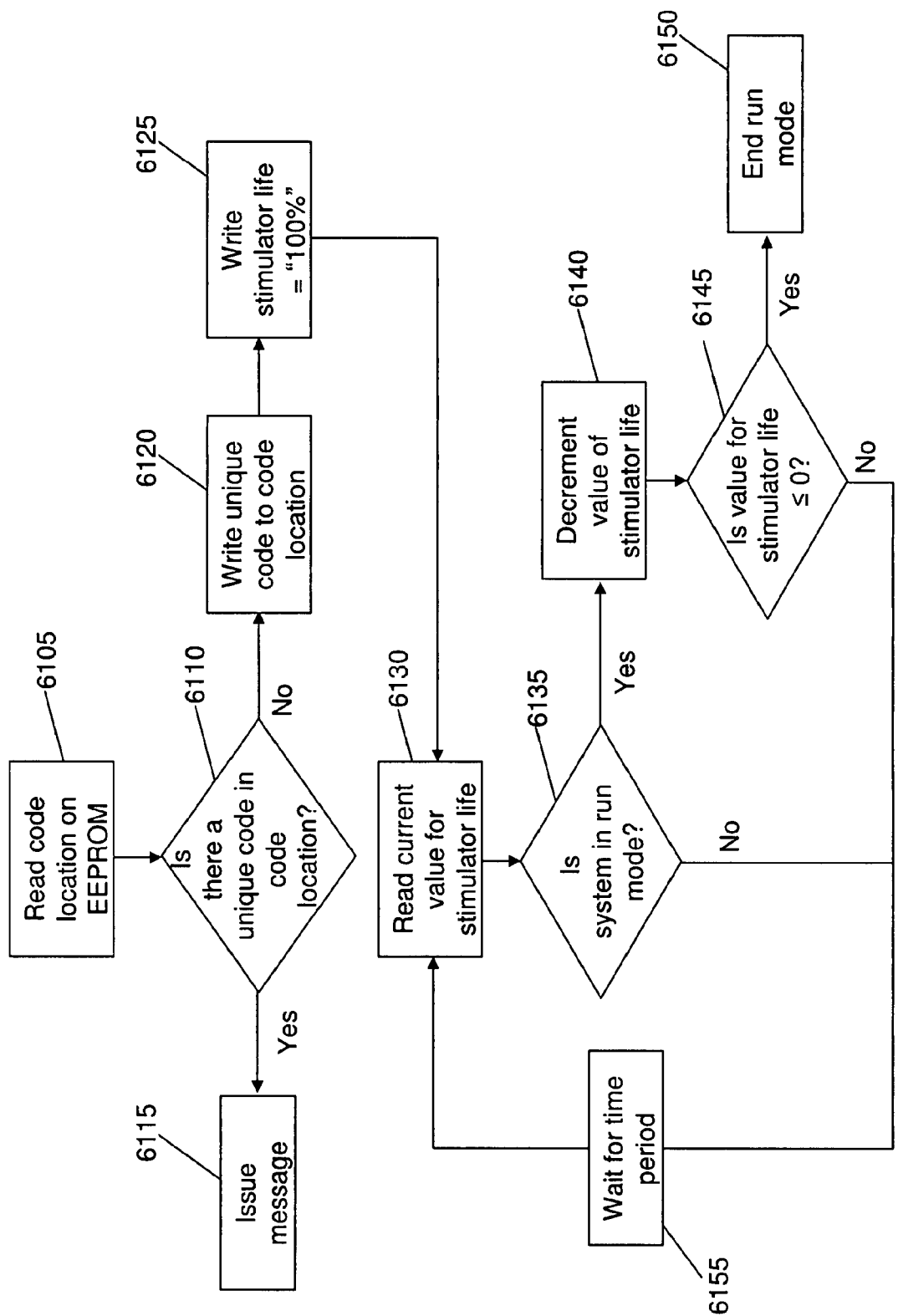
FIG. 18 illustrates an exemplary method for employing a read-write storage device for limiting use of a disposable stimulator for an exemplary embodiment of a neuro-stimulation system.

As discussed previously, the processor 2230 determines and tracks the stimulator life by reading and writing to usage data on the EEPROM 2140 of the stimulator 2100. FIG. 18 illustrates an example technique for determining and tracking the stimulator life. Initially, in step 6105, the processor 2230 reads a code location on the EEPROM 2140. Step 6110 determines whether a unique code has already been written to the code location. If the processor 2230 detects a unique code, this indicates that the stimulator 2100 has already been used, so the processor 2230 proceeds to step 6115 where a message is issued for the operator indicating that the stimulator 2100 must be replaced. If the processor 2230 does not detect a unique code, this indicates that the connected stimulator 2100 is new. In this case, in step 6120, the processor 2230 writes a unique code to the code location to indicate that the stimulator 2100 has been used. Furthermore, in step 6125, the processor 2230 records a value, e.g. "100%," on the EEPROM as the initial value for the stimulation life. Once the initial value of the stimulator life has been recorded in step 6125, the process continues to step 6130 where the processor 2230 reads the current value for the stimulator life. Step 6135 determines whether the processor 2230 is in run mode 6015. If so, in step 6140, the processor 2230 decrements the value of the stimulator life by a certain value, or percentage. Step 6145 then determines whether the current value for the stimulator life has reached zero. If the current value for the stimulator life has reached zero, in step 6150, the processor 2230 ends the run mode 6015 and issues a message for the operator indicating that the stimulator 2100 must be replaced. If the current value for the stimulator life has not reached zero, the process proceeds to step 6155 where the processor 2230 waits for a specified period of time, e.g. one minute, before proceeding again to step 6130.

As shown in FIG. 17, rather than executing step 6002, the power key 2115 and up and down adjustment keys 2116 and 2117 may be operated simultaneously in step 6003 to power up the controller 2200 and to enter a diagnostic mode where software revision, error message count, and other diagnostic information are be displayed.

As discussed previously, the graphic display 2112 may display symbols, text information, and other graphic elements which provide the operator information regarding the operation of the neuro-stimulation system 2000. During the operation of the embodiment of FIG. 16, the graphic display 2112 may show:

A battery symbol with a varying number of "bars" that indicate the approximate remaining charge in the battery 2220. For example:

| | | |
|---|---|---|
| 0 Bar: | 3.20 V to 3.29 V | |
| | (outline of symbol flashes and alert, e.g. beep, issued by sound device 2239) | |
| 1 Bar: | 3.30 V to 3.39 V | |
| 2 Bar: | 3.40 V to 3.49 V | |
| 3 Bar: | 3.50 V to 3.54 V | |
| 4 Bar: | 3.55 V to 3.59 V | |
| 5 Bar: | 3.60 V or Higher | |

A stimulator life symbol with a bar graph symbol showing, e.g. by percentage, the remaining time left in the life of the stimulator 2100, when the connector 2200 is connected the stimulator 2100. For example:

| | |
|---|---|
| 0 Bar: | less than 5% remaining |
| | (outline of symbol flashes and alert, e.g. beep, issued by sound device 2239) |
| 1 Bar: | 6% to 19% |
| 2 Bar: | 20% to 39% |
| 3 Bar: | 40% to 59% |
| 4 Bar: | 60% to 79% |
| 5 Bar: | 80% to 100% |

A stimulator time counter showing hour and minute which tracks the elapsed treatment time during run mode. When the controller is not in run mode, the hour and minute are not displayed.

Mechanical and electrical stimulation symbols which display the output levels, e.g. by percentage, from the mechanical stimulation drive 2237 and the electrical stimulation drive 2238. For example, the mechanical stimulation symbol may indicate a value from 0% to 100%, where 0% represents no application of mechanical stimulation and 100% represents the application of +/−30 V to the vibration elements 2120. The mechanical stimulation symbol may flash when the mechanical stimulation is set to 100%. Meanwhile, the electrical stimulation symbol may indicate a value of 0% to 100%, where 0% represents no application of electrical stimulation and 100% represents the application of +/−150 μA to the electrodes 2110. The electrical stimulation symbol may flash when the electrical stimulation is set to 100%.

A message area which the operator with warning messages. A corresponding alert, e.g. beep, may be issued by the sound device 2239. Any single key press turns the alert off. For example, the messages may include:

"REPLACE STIMULATOR" when the stimulator life is less than 5%

"CHARGE BATTERY" when the battery voltage is less than 3.29 V

"SKIN PREP ERROR" when a SatDetect signal is received

"DISCONNNECT ERROR" when the StimEnable line indicates that the controller 2200 and the stimulator 2100 are not coupled.

During operation, the sound device 2239 may be sounded when any key on the keypad 2114 is pressed. For example, the sound device 2239 may issue a single short beep of approximately 200 ms. As discussed previously, the sound device 2239 may also be sounded when an alert condition occurs. For example, the sound device 2239 may issue a short beep every 2 seconds. An issued alert may be acknowledged and ended by pressing any key on the keypad 2114.

As discussed previously, in the embodiment of FIG. 16, the controller 2200 may employ a rechargeable lithium ion battery pack for the power supply 2220. Therefore, in this embodiment, the neuro-stimulation system 2000 also employs a charging device for recharging the lithium ion battery pack after its charge has been depleted. Referring now to FIG. 19, a charging device, or console, 2300 is illustrated. The charging console 2300 may be formed from ABS, or a similar material. In particular, the charging console 2300 includes two cradles 2310, which may individually receive and detachably connect a controller 2200 to a separate charging circuit 2330. As shown in FIG. 19, the cradles 2310 correspond in shape with at least a part of the controllers 2200 and permit the controllers 2200 to slide into the cradles and be stably positioned. In addition to sliding the controllers 2200 into the cradles 2310, the controllers 2200 may snap into the cradles 2310 to further secure the controllers 2200 in place.

As shown in FIGS. 15B and 16, a controller 2200 may have electrical contacts 2260, which provide an electrical connection with the rechargeable battery 2220. Correspondingly, as shown in FIGS. 16 and 19, the charging console 2300 may have electrical contacts 2360, which engage the electrical contacts 2260 of the controller 2200 when the controller 2200 is stably positioned in the cradle 2310. As shown, the electrical contacts 2260 are positioned on an end surface of the controller 2200. When the end of the controller 2200 is received into the cradle 2310, the electrical contacts 2260 of the controller 2200 are aligned for conductive contact with the electrical contacts 2360 of the charging console 2300. In one embodiment, the connection between the controller 2200 and the charging console 2300 may employ pogo-pin, or similar spring-biased, contacts.

The two charging circuits 2330 are illustrated in FIG. 16. The charging circuits 2330 may be printed circuit boards based on Micrel, or equivalent, linear charging chip sets. The charging circuits 2330 may draw power from a conventional universal input wall module 2400 which is plugged into a conventional electrical wall outlet. The input voltage into the wall module 2400 may range from approximately 115 VAC to 230 VAC (min). The line may have a frequency of approximately 50 Hz to 60 Hz. The output voltage from the wall module 2400 may be approximately 5 VDC to 16 VDC with an output current of approximately 2.5 A (min).

Meanwhile, the charge current in the charging circuits 2330 may be approximately 1.2 Amps with a charge voltage of approximately 4.2 VDC. As indicated previously, in the embodiment of FIG. 16, the charge time may be approximately 4 hours. The chip set may provide for an internal shutdown when the end of the charging is reached. In addition, an LED indicator 2320 may be employed to indicate that the battery is fully charged. For instance, it may switch from an amber color to green when charging is complete.

In sum, embodiments of the neuro-stimulation system 2000 may provide a stimulator 2100 detachably coupled to a wearable controller 2200, which has a user interface 2210 including a graphic display 2212 and a keypad 2214. Preferred embodiments of the neuro-stimulation system 2000 have small, lightweight components which facilitate the application of stimulation during therapy and do not interfere with the therapy with wires, connection cables, etc. Furthermore, through the user interface 2210, embodiments may permit an operator to manually set the mechanical stimulation level and/or the electrical stimulation level. Accordingly, the vibration elements 2120 and/or electrodes 2110 may be driven to deliver stimulation that has an aperiodic waveform and/or stimulation that is subthreshold. Through the graphic display 2212, embodiments may display data, such as information on the stimulator life and battery life as well as the electrical and mechanical stimulation settings. Other embodiments may also have the ability to detect when the controller 2200 is attached to the stimulator 2100. Further embodiments have the ability to track the remaining life in the stimulator 2100.

While the controller 2200 has been described previously with respect to the stimulator 2100 as shown for example in FIG. 10A, it is understood that the controller 2200, or any aspects thereof, may be employed with other embodiments of a stimulator, or stimulator system, such as those described herein.

As described previously, the neuro-stimulation system 2000 may be applied to provide sensory enhancement stimulation during stroke rehabilitation and improve neuroplasticity, i.e. the formation of lasting functional changes in the brain. For instance, the neuro-stimulation system 2000 may be applied to a subject's arm, as illustrated in FIGS. 13A and 13B, while the arm undergoes movement associated with post-stroke rehabilitative physical therapy.

Research in clinical neuroscience has established that recovery of CNS or PNS function following injury (e.g. stroke) in many circumstances depends very strongly on the level of personal involvement and commitment to progress on the part of the sufferer. That is, if the subject is not closely involved and directly participating in the rehabilitation initiative, progress will be slowed or perhaps blocked. This need for personal motivation and participation is often cited as explanatory for the failure of "passive rehabilitation" to generate demonstrable functional outcomes.

On this basis, modern rehabilitation regimens rely increasingly on methods that directly engage the subject in the process. One example is constraint induced movement therapy (CIMT) to address hemiparesis. The subject's functioning extremity, e.g. right arm, is mechanically blocked from use for long periods of time thereby forcing the subject to use their affected extremity. Another example is customized physical therapy in which the regiment is designed specifically around tasks and abilities that are important to an individual subject. Common to these and other forms of participatory rehabilitation is that the subject's own brain is volitionally striving toward movements and capabilities of personal importance to them.

More recently, the use of virtual reality (VR) systems has gained clinical momentum as another form of participatory rehabilitation. As part of a rehabilitation regimen, subjects interact with a VR system that reacts in real time to their attempts to use affected extremities. Often the VR system is essentially a computer video game system that displays real-time images on a monitor that react to or are controlled by the subject. Such a system can be adjusted to the subject's particular circumstance to motivate certain types of attempted movements. As such, a further embodiment of the present invention combines subthreshold neuro-stimulation with VR systems. An example VR system which may be employed is the Nintendo® Wii gaming system. In this embodiment, stimulation devices, such as the devices described herein, would be placed on the skin, or implanted under the skin, and would deliver subthreshold neuro-stimulation during VR-guided activities. As is the case with other forms of rehabilitation, boosting sensory traffic during VR rehabilitation sessions improves neuroplastic remodeling outcomes. Like other embodiments described herein, this embodiment takes advantage of the interplay between subthreshold stimulation and physical rehabilitation. The individual receives the heretofore unanticipated benefit of receiving subthreshold stimulation while moving the target body segments. Since by definition susbsensory stimulation does not by itself evoke nerve activity, the embodiment employs physical activity to ultimately cause the nerve activity. The subthreshold stimulation effectively and uniquely boosts the natural sensory signaling in a fashion that is directly useful to the central nervous system.

Figure 21A:
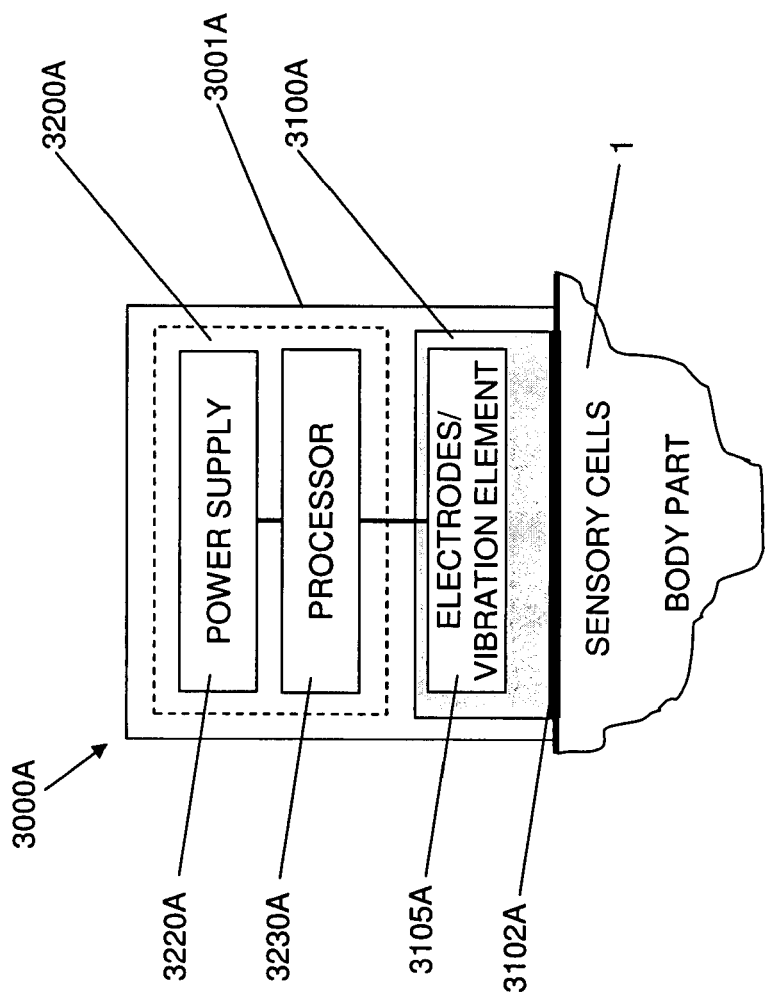
FIG. 21A illustrates an exemplary configuration for a neuro-stimulation system which may be employed to direct stimulation to any sensory cells of any body part to enhance detection of a sensory signal by a subject.

However, it is understood that the application of subthreshold neuro-stimulation for stroke rehabilitation is merely exemplary. FIG. 21A illustrates a configuration for a neuro-stimulation system 3000A which may be broadly employed to direct stimulation to any sensory cells of any body part to enhance detection of a sensory signal from the sensory cells. In particular, as shown in FIG. 21A, the neuro-stimulator system 3000A includes a stimulator 3100A which delivers stimulation to a body part 1. To control and drive the stimulator 3200A, the neuro-stimulation system 3000A includes at least a power supply 3220A and a processor 3230A, which collectively may be referred to as a controller 3200A (illustrated with a dotted line in FIG. 21A). The stimulator 3100A and controller 3200A in this embodiment may be respectively similar to the stimulator 2100 and the controller 2200 of the neuro-stimulator system 2000 described above.

The processor 3230A receives electrical power from the power supply 3220A and sends an electrical driving signal to the stimulator 3100, which is operably coupled to the processor 3230A. The stimulator 3100A includes a stimulating element 3105A. The stimulating element 3105A may include one or more electrode devices for delivering electrical stimulation, one or more vibration elements for delivering mechanical stimulation, or any combination thereof. Unlike the stimulator 2100 above, the stimulator 3100A in some embodiments may be configured to include only electrodes or only vibrating elements, rather than both forms of stimulating elements. The processor 3230 is operable to drive either electrode devices and/or a vibration elements with the electrical driving signal. The stimulator 3100A has a contact surface 3102A which is positioned to deliver stimulation from simulating element 3105A to the targeted body part 1. Accordingly, in response to the electrical driving signal, the stimulator 3100A provides stimulation to the body part 1. Preferably, the stimulation is aperiodic stimulation and/or subthreshold stimulation, providing the advantages described previously.

Although a stimulator may be detachably coupled to a controller as with the neuro-stimulator 2000 above, a stimulator and a controller may also be integrally or fixedly coupled to each other. As illustrated with the embodiment of FIG. 21A, the stimulator 3100A may be included with the processor 3230A and the power supply 3220A in a single application body, or housing, 3001A. This single application body 3001A may then be applied to the body part 1 to deliver the stimulation.

Of course, different components of a neuro-stimulation system may be organized and coupled in any number of combinations and housed in any number of devices or bodies. Thus, referring to FIG. 21B, a neuro-stimulation system 3000B is illustrated, where a power supply 3220B is separated from an application body 3001B housing a stimulator 3100B and a processor 3230B. For example, the power supply 3220B in FIG. 21B may be a battery pack or a conventional electrical outlet that is detachably coupled to the application body 3001B. The application body 3001B is positioned to deliver stimulation to a body part 1 through a contact surface 3102B.

Figure 21B:
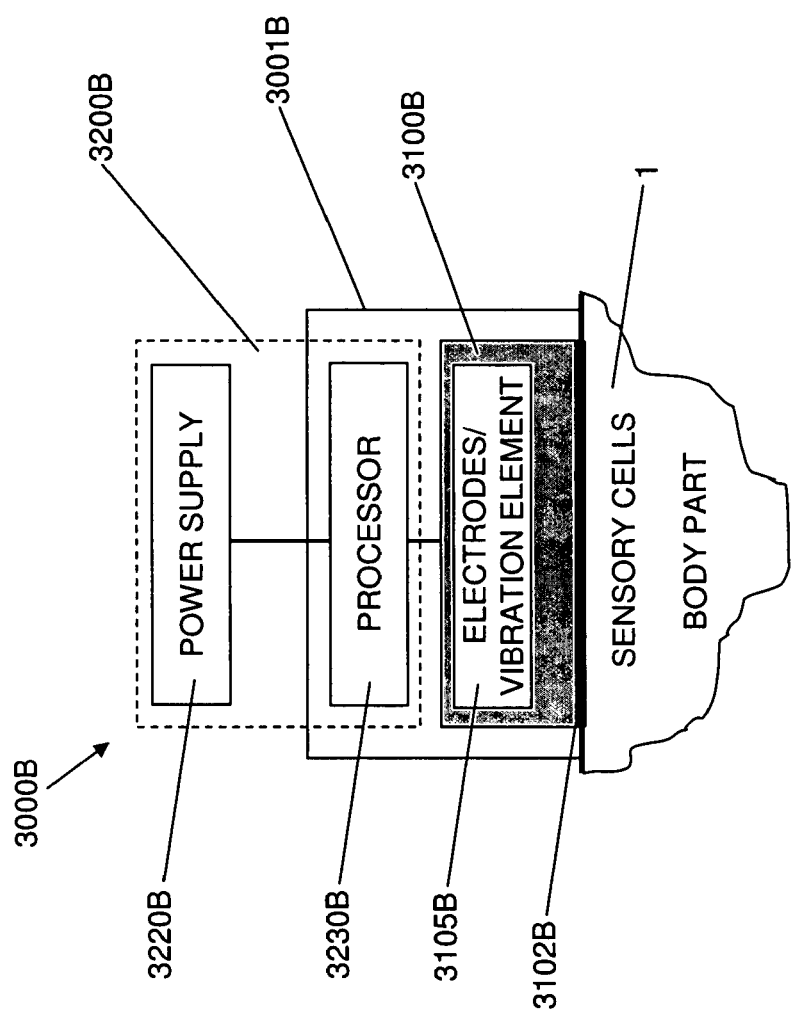
FIG. 21B illustrates another exemplary configuration for a neuro-stimulation system which may be employed to direct stimulation to any sensory cells of any body part to enhance detection of a sensory signal by a subject.
Figure 21C:
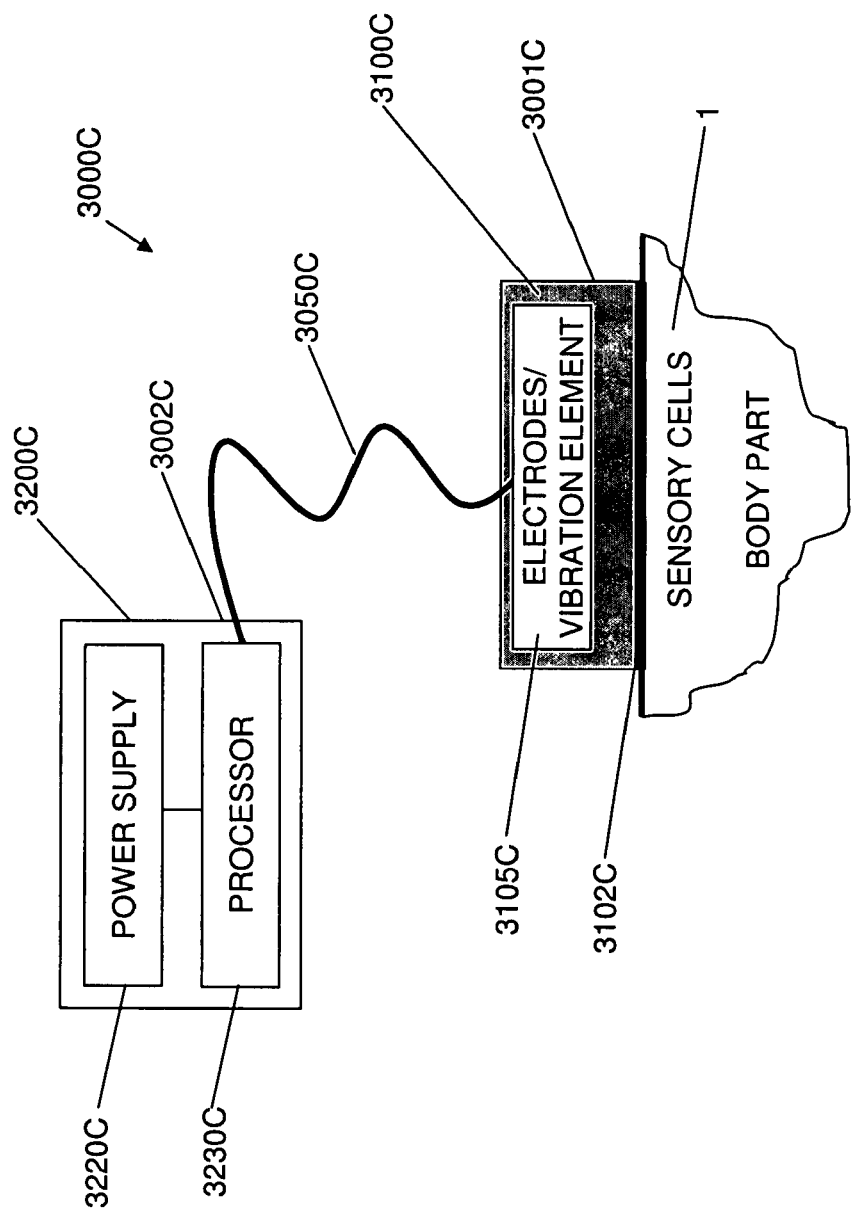
FIG. 21C illustrates yet another exemplary configuration for a neuro-stimulation system which may be employed to direct stimulation to any sensory cells of any body part to enhance detection of a sensory signal by a subject.

Meanwhile, FIG. 21C illustrates a neuro-stimulation system 3000C, where a stimulator 3100C is housed in an application body 3001C while a controller 3200C, i.e. a power supply 3220C and a processor 3230C, is in a separate controller housing 3002C. The stimulator 3100 is detachably or fixedly coupled to the controller 3200C via a coupling mechanism 3050C, such as a flexible cable, that enables the processor 3230C to deliver a driving signal to a stimulating element 3105C from a distance. The application body 3001C is positioned to deliver stimulation through a contact surface 3102C. Advantageously, because the application body 3001C does not house the power supply 3230 and the processor 3230, the application body 3001C may be sized or configured to enable easy handling and positioning on a body part 1 for the delivery of stimulation, while the controller 3200 is placed conveniently at a distance.

Attachment elements, such as an elastic strap or, a strap with snaps, hook-and-loop fasteners, or other fasteners may be employed to secure the stimulator and/or the controller into desired positions. In the embodiment of FIG. 22C, an attachment element may position the application body 3001C over the body part 1 targeted for stimulation, while another attachment element may secure the controller housing 3002C to another part of the body for comfort and convenience.

FIGS. 21A-C illustrate contact surfaces that make direct contact with the body part 1, for example at a skin surface, to deliver the desired stimulation. However, the actual stimulating element, e.g. electrode and/or vibration element, does not have to contact the body part 1 directly. Rather, as shown in FIG. 21A, the electrical or mechanical stimulation may be transmitted from the stimulating element 3105A within the application body 3001A to the contact surface 3102A. For example, the stimulating element 3105A may be embedded within the application body 3001A, while the outer contact surface 3102A actually makes contact with the body part 1. In this example, the application body 3001A, or some structure thereof, may be formed from a material that allows an electrical signal or vibration to travel from the stimulating element 3105A to the contact surface 3102A.

Various applications of the neuro-stimulation systems, as shown in FIGS. 21A-C, may be employed to deliver sensory enhancing stimulation to any body part 1.

In one embodiment, the body part 1 includes aspects of the body that aid in swallowing, including the tongue, pharynx, and esophagus, and a neuro-stimulation system is applied to improve swallowing function, especially for patients suffering from dysphagia. As such, an application body housing a stimulator may be applied externally across the neck to deliver electrical or mechanical stimulation to the tongue, pharynx, and/or esophagus. Alternatively, a small application body may be applied in the throat, especially for patients with severe or chronic disorders. The application of stimulation enhances the sensory information required by the swallowing function and improves control of this swallowing function. In some embodiments, the swallowing function to be improved is the sensation of the presence of a solid or liquid bolus in the throat. In other embodiments, the swallowing function to be improved is timing of swallowing muscle contraction relative to movement of solid or liquid bolus in the throat. In further embodiments, the swallowing function to be improved is the timing of the closure of the trachea relative to the movement of solid or liquid bolus in the throat.

In another embodiment, the body part 1 is the heart and a neuro-stimulation system is applied to improve cardiac function for patients who suffer from congestive heart failure. A key function of healthy heart muscle is the regulation of contractions based on its internal stretch (from filling), which uses mechanoreceptors similar to muscle spindles found in striated muscle. Poor cardiac function results when this mechanism is compromised. As such, an application body housing a stimulator may be applied outside or inside the chest cavity to deliver stochastic resonance stimulation to the heart muscle, making the heart more resistant to overfilling, which may improve cardiac function in patients suffering from congestive heart failure.

In an additional embodiment, the body part 1 includes the lungs, and a neuro-stimulation system may be applied to improve lung sensation/function in asthmatic patients. An application body is noninvasively applied to the surface of the chest where sub-threshold stimulation may be most effectively transferred to the intercostals muscle. A stimulator in the application body may provide electrical and/or mechanical stimulation from any number of electrodes and/or vibrating elements, which are driven by a controller. In a particular embodiment, the configuration of FIG. 21C may be employed where the controller 3200C is kept in a controller housing 3002C separated by a distance from the application body 3001C. The controller housing 3002C, for example, may approximately have the size of a pack of cigarettes and may be secured to an attachment element, such as a wrist band, via a belt-clip. Thus, the coupling mechanism 3050C may include control and signal wires which extend run from the controller housing 3002C to the application body 3001C positioned at the chest. Accordingly, the stimulation from the stimulator 3100C increases the awareness of lung state during asthmatic attacks and offers better control of breathing during these attacks. The expansion and/or contraction of the lung thus increases with the stimulation of the intercostals muscle in the chest region.

In yet another embodiment, a neuro-stimulation system may be applied as a therapy for patients suffering from Parkinson's disease. For example, an application body housing a stimulator may be applied to an affected muscle to deliver a noninvasive, sub-threshold electrical and/or mechanical stimulation to improve the patient's ability to sense muscle position and offer better control of muscle flexion. Thus, unwanted motions or movements in affected muscles or muscle groups associated with Parkinson's disease are minimized.

In a further embodiment, a neuro-stimulation system may be applied to manage pain. Contrary to Transcutaneous Electrical Nerve Stimulation (TENS) which manages pain by overloading a sensory channel, the neuro-stimulation system in this embodiment applies subthreshold stimulation in a less invasive technique to ground the sensory channel instead of overloading it. In some cases, the pain is caused by musculoskeletal hyperextension or excursion resulting from proprioceptive deficit in the body part. For example, back pain may be caused by a proprioceptive deficit in a person's trunk and in one embodiment, neuro-stimulation may be applied to increase stability and strength to manage this back pain.

In yet a further embodiment, the body part 1 is the forehead and, a neuro-stimulation system may be applied to reduce chronic/tension headaches. For instance, an application body housing a stimulator may be applied noninvasively to affected muscles or muscle groups in the forehead area where sub-threshold stimulation may be applied to control tension and relieve chronic pain due to uncontrollable muscle spasms. The stimulator in the application body may provide electrical and/or mechanical stimulation from any number of electrodes and/or vibrating elements, which are driven by a controller.

In another embodiment, the body part 1 employs a prosthetic device, and a neuro-stimulation system may be applied to improve function with the prosthetic device. Generally, sensors on prostheses (proprioception, pressure, etc.) are introduced to pectoral sensory pathways and successfully decoded by the brain. The brain forms new neural connections to process and use the information from the sensors on the prosthesis. This embodiment applies stochastic resonance stimulation in conjunction with the signals from the sensors to promote neural development and to increase the sensitivity of the pectoral nerves to these signals. For example, a stimulator may be incorporated with the prosthetic device to deliver electrical and/or mechanical stimulation during use of the prosthetic device.

In yet another embodiment, a neuro-stimulation system may be applied to reduce phantom limb sensations by those who have lost a limb. In particular, an application body housing a stimulator may be applied to deliver stochastic resonance stimulation to severed nerves associated with the missing limb or to surrounding intact nerves. Such stimulation encourages the brain to dissociate the neural connections causing phantom limb or phantom pain sensations. Applying the stimulation to severed nerves provides the brain with greater information about the current state of the body, alerting the brain of the loss of the limb. Applying the stimulation to surrounding intact nerves encourages the brain to focus on the neural connections that are not associated with the damage.

In a further embodiment, a neuro-stimulation system may be employed for strength training in patients with a sensory deficit. Recent studies have shown that people who actually did certain physical exercises, e.g. finger exercises, gained no more strength than people who did no physical exercise but simply thought about doing the exercise for the same amount of time. Thus, a stimulator may deliver stochastic resonance stimulation to the joints of a patient with a sensory deficit. Such stimulation may result in a faster increase strength by making the brain more aware of body movement.

In yet a further embodiment, a neuro-stimulation system may be employed as a therapy for arousal dysfunction. An application body housing a stimulator may be applied to appropriate areas to deliver stimulation and improve sexual sensory function in these areas.

In another embodiment, the body part 1 may be a finger tip that is used to read Braille, and a neuro-stimulation system may be employed to improve sensory function corresponding to Braille reading ability. The contact surface for delivery of stimulation is a surface with Braille which is then coupled to a stimulator. Stochastic resonance stimulation applied to finger tips has been shown to improve detection of small stimuli. The use of the Braille system for vision impaired reading of text requires precision on the part of the reader to identify small raised dots on paper. This effort can be difficult when the reader is new to Braille, the print is small, or the pages are worn. Therefore, the stimulator 3100 of the neuro-stimulator system 3000 may provide stochastic resonance stimulation to the finger tip to improve a person's ability to detect the raised dots of Braille text. This embodiment is an example of an external device, e.g. the Braille surface, that is provided with a stimulation source and when a body part, e.g. the finger tip, contacts or interacts with the external device, the stimulation source applies the stimulation to sensory cells of the body part to enhance sensory function associated with the body part. Other examples of such external devices are provided herein.

In yet another embodiment, the body part 1 may be the nasal septum while the contact surface may be sized and configured to accommodate stable positioning on the nasal septum. As such, the neuro-stimulation system may be applied to improve the olfactory function of a human. The application of a sub-threshold electrical and/or mechanical signal to the nasal septum increases sensation and provides an improvement in the sense of smell. Therefore, one or more stimulators are positioned to apply a sub-threshold signal to the nasal septum. Preferably, to promote comfort and ease of use, only a small stimulator is positioned on the nasal septum while the controller is positioned elsewhere. Thus, referring to FIG. 21C, the stimulator 3100C may be housed in an application body 3001C and the controller 3200C may have a separate housing 3002C. In particular, the housing 3002C for the controller 3200C may be shaped like a cigarette pack, which can conveniently placed in a shirt pocket or worn on the waist via a belt clip.

Similarly, yet another embodiment of the neuro-stimulator may be employed to improve the olfactory function of a canine Canines are often used in tasks requiring the use of smell as a way of locating an object or person. These tasks include searching for missing persons, detecting explosives, and locating contraband such as drugs. Thus, in this application, referring to FIG. 21C, the body part 1 is a canine's nose, and the application body 3001C housing the stimulator 3100C is configured to fit across the nose with a first attachment element while the controller 3200C in a housing 3002C may be separately mounted on another part of the canine with a second attachment element, such as a dog collar.

Further embodiments of the neuro-stimulator system may be employed to improve auditory sensory function and detection of audio signals. In some embodiments, the neuro-stimulation system provides an electrical or audio noise signal with hearing assistive devices, e.g. hearing aids, cochlear implants, etc., to improve the auditory function of their users and the effectiveness of these devices. With such embodiments, the hearing assistive device may act as the application body 3001A which houses the complete neuro-stimulation system 3000A, as depicted in FIG. 21A. When employed to improve auditory function, the body part 1 includes aspects of the auditory system which affect the auditory nerves, while the stimulator sends a signal that may be received by the auditory system. Although FIGS. 21A-C illustrate a contact surface positioned in direct contact with the body part 1, it is understood that other embodiments may deliver stimulation to the body part 1 without direct contact. For example, a stimulation in the form of sound may be delivered across a space between the stimulator 3100 and the body part 1. As such, to improve a subject's ability to hear particular sounds, the neuro-stimulation system 3000 may combine a noise signal with the particular sounds that are transmitted over a space to the subject. For example, audio recordings that require transcription may be combined with a noise signal to improve the transcriber's ability to detect the audio. In another example, audio signals from a sonar system may be combined with a noise signal to improve the monitor's ability to detect faint sonar signals.

Another embodiment of the neuro-stimulation system is employed to improve visual function, where the body part 1 is the eye. In this embodiment, the neuro-stimulation system may add noise to the visual signal, or light, from the object being viewed. For example, vision is used extensively in the scrutiny of images (x-ray, etc.) for medical diagnosis or in the screening of packages and contents for security purposes. The neuro-stimulation system may generate noise in a band of visual wavelengths, and the noise may be transmitted along with the images, such as those from a security screening monitor. The stimulation from the transmitted noise may improve the ability to detect weak information being received by the eye. Similar to the improvement of auditory function described previously, stimulation in the form of visual signals may be delivered across a space between the stimulator and the body part 1.

Yet another embodiment of the neuro-stimulation system is employed to improve tasting function, where the body part 1 is a tongue. A discriminating palate is key to the process of taste testing used in the culinary arts, brewing, etc. As such, the contact surface of a stimulator may be placed into contact with areas of the tongue surface to deliver electrical or mechanical stimulation from the simulating element 3105 to the gustatory (taste nerve) cells. Such stimulation improves the ability of the subject to taste. Due to relatively limited access to the tongue inside the mouth, referring to FIG. 21C the stimulator 3100C may employ an application body 3001C that is separate from the housing 3002C of the controller 3200C. Thus, components of the neuro-stimulation system 3000C, i.e. the controller 3200C, do not have to be positioned on the tongue, and the application body 3001C may be conveniently sized and configured to be easily and comfortably positioned on the tongue inside the mouth.

Figure 22A:
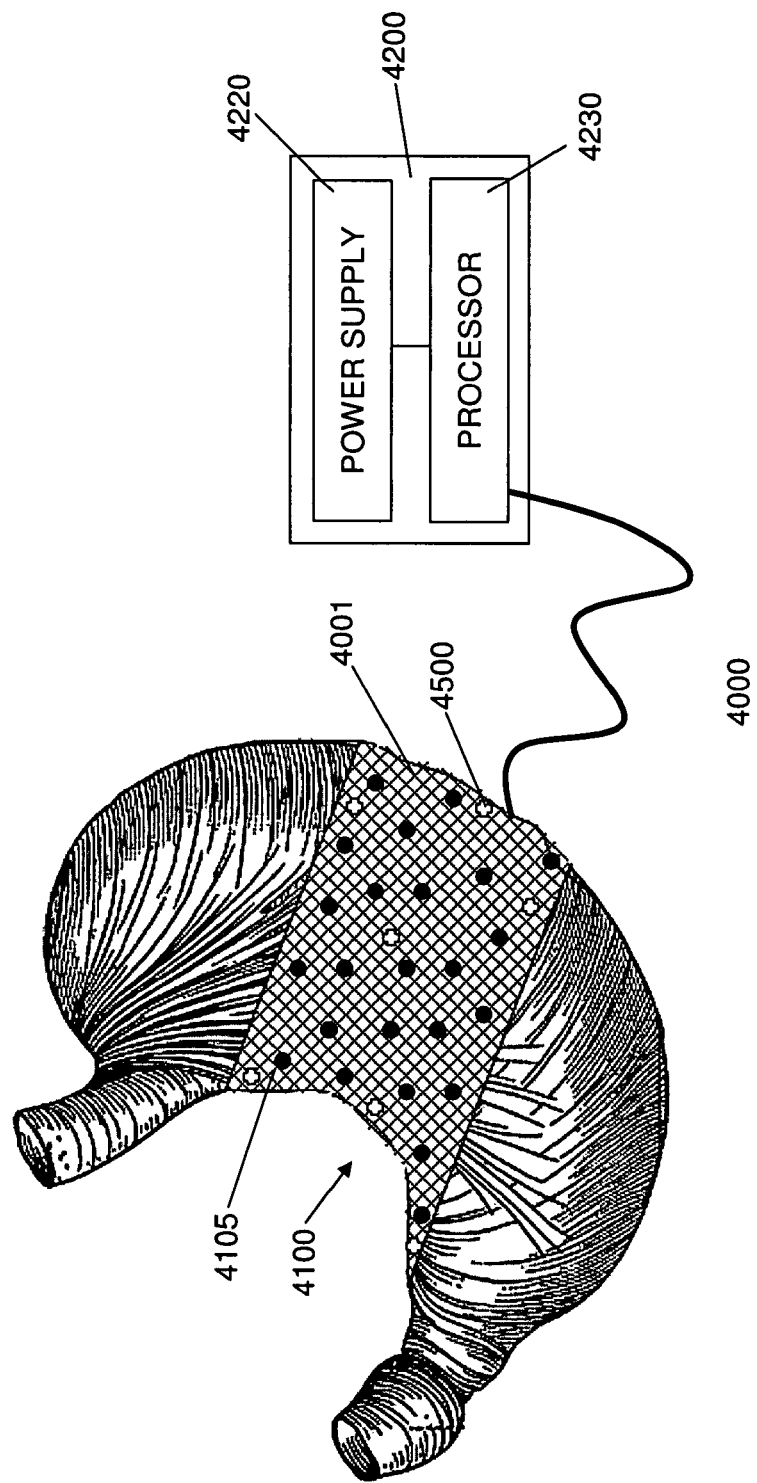
FIG. 22A illustrates an exemplary neuro-stimulation system for application to an internal organ.
Figure 22B:
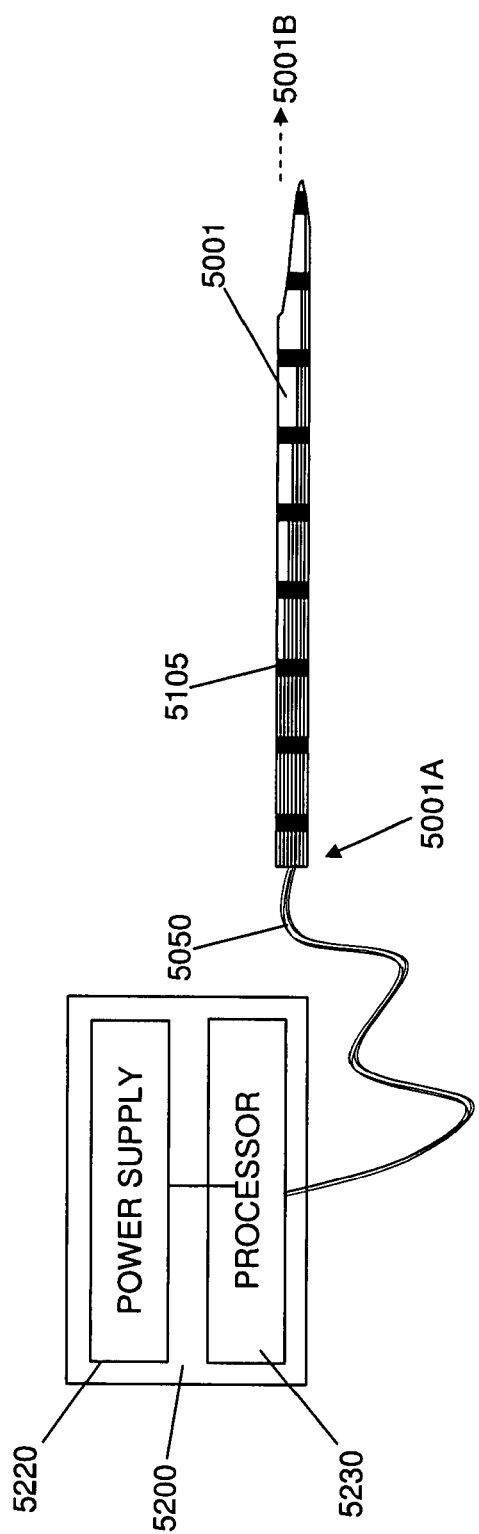
FIG. 22B illustrates an exemplary neuro-stimulation system having a catheter-like configuration with a plurality of electrodes, each of which may be selectively driven.

While FIGS. 21A-C illustrate general configurations for a neuro-stimulation system, FIGS. 22A-B illustrate specific example embodiments of neuro-stimulation systems that may be applied to address particular medical conditions. As illustrated in FIG. 22A, a neuro-stimulation system 4000 is employed to deliver electrical stimulation, stochastic resonance or otherwise, to an internal organ. Use of this embodiment may include applying stimulation to: the bladder and colon as therapy for incontinence; the stomach as therapy for disorders involving the feeling of fullness; the gall bladder as therapy for bile secretion; or the esophagus, intestines, urethra, and bile duct for peristaltic encouragement or improvement. As shown in FIG. 22A, the application body 4001 of the stimulator 4100 is an expandable material, such as a mesh, which is positioned over an organ, or body part, 1. The application body 4001 accommodates expansion and contraction of the organ during normal function, e.g. during filling of the bladder, etc. The stimulating elements 4105 may be electrodes which are distributed over the stimulation application body 4001 to provide diffuse application of electrical stimulation over targeted surfaces of the organ 1. During application, the expandable material 4001 is trimmed to accommodate the size of the targeted organ 1 and may be sutured at selected points to the surface of the organ 1. In addition to serving as attachment elements 4500, the suture points help keep the application body 4001 in tension across the organ 1. The stimulator 4100 may be composed of one or more resorbable materials, including resorbable conducting metals or polymers for the electrodes 4105. As such, additional procedures to remove the stimulator 4100 are unnecessary. As further illustrated in FIG. 22A, the stimulator 4100 is coupled to a remote controller 4200, which includes a power source 4220 and processor 4230 to drive the electrodes and deliver electrical stimulation to the organ 1.

FIG. 22B illustrates yet another embodiment of the neuro-stimulator 5000 which may deliver stimulation to multiple points of a body part 1. In particular, FIG. 21E shows a stimulation application body 5001 which has a catheter-like structure having a proximal end 5001A and a distal end 5001B. The stimulator 5100 may be applied subcutaneously. The stimulating elements 5105 include a plurality of electrodes which are spaced longitudinally along the stimulation application body 5001 to provide electrical stimulation to multiple parts of a body part 1. Each stimulating element 5105 receives an electrical signal via a conductor, such as a wire, that extends longitudinally to the proximal end 5001A which is operably coupled to a controller 5200. The controller 5200 has a processor 5230 which delivers electrical signals from a power source 5220 to selected electrodes along the application body 5001. As such, the processor 5230 can define any combination and sequence of electrical stimulation sources and sinks along the application body 5001. Thus, the neuro-stimulation system 5100 in FIG. 22B provides a customizable configuration which facilitates application of stimulation to different regions of the body and which may suit the varying needs of patients.

Although an application body in a neuro-stimulation system may be specially shaped or configured to accommodate a particular body part to deliver stimulation, other neuro-stimulation systems may incorporate a stimulator into the structure of another device, such as a consumer product, which is initially intended to provide other functions outside of stimulation delivery. As such, the device, or a part thereof, becomes an application body for stimulation delivery. Combining a neuro-stimulation system with another device may improve an operator's ability to use the device or may enhance the effectiveness of the device. The prosthetic device combined one or more simulators or the hearing assistive device combined with one or more stimulators, described previously, provide examples of neuro-stimulation systems that incorporate a stimulator within another device.

In another example, a stimulator may be incorporated into a gun or rifle to deliver stimulation that improves a person's ability to shoot a gun. Accurate gun shooting is required especially in long range targeting, such as sniping. One aspect of accurate gun shooting is the ability of the shooter to control the precise action of a hair trigger and maintain gun stock position relative to the shooter's body as the projectile is fired from the gun. An embodiment of a neuro-stimulation system may incorporate a stimulator with a vibrating stimulating element into the trigger and/or the gun stock. As such, the gun may provide stochastic resonance stimulation to a trigger finger through the gun trigger and/or to a region of the body between the arm and torso through the gun stock. In this example, parts of the gun act as application bodies for the delivery of sensory enhancement stimulation.

In yet another example, an embodiment of a neuro-stimulation system may incorporate stimulators into a waterproof shower mat to deliver stochastic resonance stimulation to a person's feet and reduce the likelihood that the person will fall in the shower. In a particular embodiment, the shower mat may be battery powered and may employ force sensors in the mat to determine where the foot is making contact and allow focused delivery of stimulation to areas of the mat where the person is standing. As discussed previously, the delivery of such stimulation to the feet enhances human balance, reducing the likelihood of falling.

In a further example, an embodiment of a neuro-stimulation system may incorporate a stimulator into a sock, which delivers stochastic resonance stimulation to a foot. The stimulating element may be formed from a flexible polymer which vibrates from an electrical signal received from a controller coupled to the stimulator. The sock conforms to the shape of the foot and remains in contact with areas of the bottom of the foot without requiring any load on the bottom of the sock. Advantageously, the sock may be used by diabetics and other similar individuals who are not physically active and do not spend a significant amount of time on their feet to place a load on the sock. Even while seated or lying down, the sock maintains contact with the soles of the foot, so that the foot receives the effect of stimulation delivered by the stimulator. The benefits of applying such a stimulation to the bottom of the foot were described previously. In a particular embodiment, the controller may deliver different driving signals to the stimulating element depending on the load on the sock, i.e. load differences between standing and sitting. As such, a sensor may be employed to indicate the loading state of the sock to the controller, so that the driving signal may be correspondingly adjusted.

Therefore, embodiments of the present invention provide a variety of configurations and shapes for delivering controlled stimulation to any sensory cells of any body part according to a variety of therapeutic applications. In some preferred embodiments, subthreshold and/or aperiodic stimulation is applied to enhance transmission and detection of sensory information. In some applications, this results in improved neuromuscular performance.

It is understood that while the embodiments described herein may provide subthreshold and/or a periodic stimulation, the embodiments may also be capable of providing supra-threshold stimulation. In particular, supra-threshold stimulation may be applied as technique to determine, e.g. iteratively, a person's sensory threshold during initial system setup and before the subthreshold and/or a periodic stimulation is applied.

However, the foregoing specific embodiments of the present invention as set forth in the specification herein are for illustrative purposes only. Various deviations and modifications can be made within the spirit and scope of this invention, without departing from the main theme thereof. It will be appreciated by persons skilled in the art that the present invention is not limited by what has been particularly shown and described herein above. While the present invention has been described in connection with a number of exemplary embodiments, and implementations, the present inventions are not so limited, but rather cover various modifications, and equivalent arrangements, which fall within the purview of prospective claims. All dimensions, and the like, provided herein are exemplary.

What is claimed is:

1. A method, comprising:
    generating at least one bias signal using a system for providing sub-threshold stimulation, the system comprising an application body with a stimulating element generating the at least one bias signal;
    inputting the at least one bias signal to at least one sensory cell area of a chest region of a subject while the subject is undergoing lung function, such that the sub-threshold stimulation is transferred to intercostal muscles of the subject; and
    inducing a neuroplastic response in the nervous system of the subject by inputting the at least one bias signal for at least a period of time whereby the subject's lung function is improved by increasing an expansion or a contraction of lungs of the subject during the subject's lung function.

2. The method according to claim 1 wherein the at least one bias signal is continuously applied to the chest region of the subject.

3. The method according to claim 1 wherein the at least one bias signal is non-continuously applied to the chest region of the subject.

4. The method according to claim 1 wherein the at least one bias signal is a modulated bias signal applied to the chest region of the subject.

5. The method according to claim 1, wherein the at least one bias signal is a modulated bias signal that is continuously applied to the chest region of the subject.

6. The method according to claim 1, wherein the at least one bias signal is a modulated bias signal that is non-continuously applied to the chest region of the subject.

\* \* \* \* \*